US007780722B2

(12) United States Patent
Thielen et al.

(10) Patent No.: US 7,780,722 B2
(45) Date of Patent: Aug. 24, 2010

(54) VENOUS VALVE APPARATUS, SYSTEM, AND METHOD

(75) Inventors: Joseph M. Thielen, Buffalo, MN (US); Jason P. Hill, Cottage Grove, MN (US); Susan M. Shoemaker, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 322 days.

(21) Appl. No.: 11/052,588

(22) Filed: Feb. 7, 2005

(65) Prior Publication Data

US 2006/0178729 A1 Aug. 10, 2006

(51) Int. Cl.
*A61F 2/06* (2006.01)
(52) U.S. Cl. .................................... 623/1.24
(58) Field of Classification Search ........ 623/1.11–2.42
See application file for complete search history.

(56) References Cited

U.S. PATENT DOCUMENTS

| 3,671,979 | A |   | 6/1972  | Moulopoulos ................ 3/1 |
|-----------|---|---|---------|---------------------------------|
| 3,867,923 | A | * | 2/1975  | West ...................... 600/579 |
| 4,291,420 | A |   | 9/1981  | Reul ........................ 3/1.5 |
| 4,787,901 | A | * | 11/1988 | Baykut .................. 623/1.26 |
| 4,872,874 | A |   | 10/1989 | Taheri ...................... 623/1 |
| 4,935,030 | A |   | 6/1990  | Alonso ...................... 623/2 |
| 4,994,077 | A |   | 2/1991  | Dobben ...................... 623/2 |
| 5,002,567 | A | * | 3/1991  | Bona et al. ............... 623/2.22 |
| 5,141,491 | A |   | 8/1992  | Bowald ...................... 604/22 |
| 5,163,953 | A |   | 11/1992 | Vince ........................ 623/2 |
| 5,219,355 | A |   | 6/1993  | Parodi et al. ............. 606/191 |
| 5,254,127 | A | * | 10/1993 | Wholey et al. ............. 606/153 |
| 5,327,774 | A |   | 7/1994  | Nguyen et al. .............. 73/37 |
| 5,332,402 | A |   | 7/1994  | Teitelbaum .................. 623/2 |
| 5,370,685 | A |   | 12/1994 | Stevens ...................... 623/2 |
| 5,411,552 | A | * | 5/1995  | Andersen et al. .......... 623/2.18 |
| 5,469,868 | A | * | 11/1995 | Reger ...................... 128/898 |
| 5,480,423 | A |   | 1/1996  | Ravenscroft et al. .......... 623/1 |
| 5,500,014 | A |   | 3/1996  | Quijano et al. ............... 623/2 |
| 5,545,214 | A |   | 8/1996  | Stevens ...................... 623/2 |
| 5,554,185 | A |   | 9/1996  | Block et al. .................. 623/2 |
| 5,643,208 | A |   | 7/1997  | Parodi ....................... 604/96 |
| 5,693,087 | A |   | 12/1997 | Parodi ........................ 623/1 |
| 5,713,953 | A | * | 2/1998  | Vallana et al. ............. 623/2.15 |
| 5,716,370 | A |   | 2/1998  | Williamson, IV et al. ... 606/153 |
| 5,735,859 | A | * | 4/1998  | Fischell et al. ............. 606/108 |
| 5,741,326 | A |   | 4/1998  | Solovay ....................... 623/1 |

(Continued)

FOREIGN PATENT DOCUMENTS

EP 0 380 666 8/1990

(Continued)

OTHER PUBLICATIONS

US 6,673,110, 01/2004, Alfieri et al. (withdrawn)
US 6,723,117, 04/2004, Menz et al. (withdrawn)

*Primary Examiner*—David Isabella
*Assistant Examiner*—Ann Schillinger
(74) *Attorney, Agent, or Firm*—Brooks, Cameron & Huebsch, PLLC

(57) ABSTRACT

A venous valve with a frame and a cover on the frame for unidirectional flow of a liquid through the valve.

38 Claims, 12 Drawing Sheets

U.S. PATENT DOCUMENTS

| | | | |
|---|---|---|---|
| 5,741,333 A | 4/1998 | Frid | 623/12 |
| 5,800,506 A | 9/1998 | Perouse | 623/1 |
| 5,824,061 A | 10/1998 | Quijano et al. | 623/2 |
| 5,879,320 A | 3/1999 | Cazenave | 604/8 |
| 5,895,419 A | 4/1999 | Tweden et al. | 623/2 |
| 5,910,170 A | 6/1999 | Reimink et al. | 623/2 |
| 6,010,531 A | 1/2000 | Donlon et al. | 623/2 |
| 6,042,607 A * | 3/2000 | Williamson et al. | 623/2.11 |
| 6,117,165 A * | 9/2000 | Becker | 623/1.15 |
| 6,139,575 A * | 10/2000 | Shu et al. | 623/2.12 |
| 6,287,334 B1 | 9/2001 | Moll et al. | 623/1.24 |
| 6,312,447 B1 | 11/2001 | Grimes | 606/219 |
| 6,355,030 B1 | 3/2002 | Aldrich et al. | 606/28 |
| 6,402,780 B2 | 6/2002 | Williamson, IV et al. | 623/2.11 |
| 6,419,696 B1 | 7/2002 | Ortiz et al. | 623/2.37 |
| 6,425,916 B1 * | 7/2002 | Garrison et al. | 623/2.11 |
| 6,440,164 B1 * | 8/2002 | DiMatteo et al. | 623/1.24 |
| 6,451,054 B1 | 9/2002 | Stevens | 623/2.11 |
| 6,454,799 B1 | 9/2002 | Schreck | 623/2.18 |
| 6,461,366 B1 | 10/2002 | Seguin | 606/144 |
| 6,503,272 B2 | 1/2003 | Duerig et al. | 623/1.24 |
| 6,508,833 B2 * | 1/2003 | Pavcnik et al. | 623/1.15 |
| 6,564,805 B2 | 5/2003 | Garrison et al. | 128/898 |
| 6,569,196 B1 | 5/2003 | Vesely | 623/2.14 |
| 6,602,286 B1 | 8/2003 | Strecker | 623/1.24 |
| 6,629,534 B1 | 10/2003 | Dell et al. | 128/898 |
| 6,635,085 B1 | 10/2003 | Caffey et al. | 623/2.1 |
| 6,666,885 B2 | 12/2003 | Moe | 623/2.12 |
| 6,666,886 B1 | 12/2003 | Tranquillo et al. | 623/2.42 |
| 6,669,725 B2 | 12/2003 | Scott | 623/2.36 |
| 6,673,109 B2 | 1/2004 | Cox | 623/2.12 |
| 6,676,698 B2 | 1/2004 | McGuckin, Jr. et al. | 623/1.24 |
| 6,676,702 B2 | 1/2004 | Mathis | 623/2.36 |
| 6,682,558 B2 | 1/2004 | Tu et al. | 623/2.11 |
| 6,682,559 B2 | 1/2004 | Myers et al. | 623/2.13 |
| 6,685,739 B2 | 2/2004 | DiMatteo et al. | 623/1.24 |
| 6,692,512 B2 | 2/2004 | Jang | 606/200 |
| 6,695,866 B1 | 2/2004 | Kuehn et al. | 606/213 |
| 6,695,878 B2 | 2/2004 | McGuckin, Jr. et al. | 623/1.19 |
| 6,709,456 B2 | 3/2004 | Langberg et al. | 623/2.37 |
| 6,709,457 B1 | 3/2004 | Otte et al. | 623/2.4 |
| 6,716,241 B2 | 4/2004 | Wilder et al. | 623/1.24 |
| 6,716,244 B2 | 4/2004 | Klaco | 623/2.4 |
| 6,719,767 B1 | 4/2004 | Kimblad | 606/151 |
| 6,719,784 B2 | 4/2004 | Henderson | 623/1.44 |
| 6,719,786 B2 | 4/2004 | Ryan et al. | 623/2.11 |
| 6,719,787 B2 | 4/2004 | Cox | 623/2.12 |
| 6,719,788 B2 | 4/2004 | Cox | 623/2.12 |
| 6,719,789 B2 | 4/2004 | Cox | 623/2.13 |
| 6,719,790 B2 | 4/2004 | Brendzel et al. | 623/2.4 |
| 6,723,038 B1 | 4/2004 | Schroeder et al. | 600/16 |
| 6,723,122 B2 | 4/2004 | Yang et al. | 623/2.1 |
| 6,723,123 B1 | 4/2004 | Kazatchkov et al. | 623/2.2 |
| 6,726,715 B2 | 4/2004 | Sutherland | 623/2.1 |
| 6,726,716 B2 | 4/2004 | Marquez | 623/2.36 |
| 6,726,717 B2 | 4/2004 | Alfieri et al. | 623/2.36 |
| 6,730,118 B2 | 5/2004 | Spenser et al. | 623/1.24 |
| 6,730,121 B2 | 5/2004 | Ortiz et al. | 623/2.17 |
| 6,730,122 B1 | 5/2004 | Pan et al. | 623/2.33 |
| 6,736,845 B2 | 5/2004 | Marquez et al. | 623/2.11 |
| 6,736,846 B2 | 5/2004 | Cox | 623/2.12 |
| 6,749,630 B2 | 6/2004 | McCarthy et al. | 623/2.36 |
| 6,752,813 B2 | 6/2004 | Goldfarb et al. | 606/139 |
| 6,752,828 B2 | 6/2004 | Thornton | 623/1.24 |
| 6,755,857 B2 | 6/2004 | Peterson et al. | 623/2.17 |
| 6,761,734 B2 | 7/2004 | Suhr | 623/1.35 |
| 6,761,735 B2 | 7/2004 | Eberhardt et al. | 623/2.1 |
| 6,764,494 B2 | 7/2004 | Menz et al. | 606/159 |
| 6,764,508 B1 | 7/2004 | Roehe et al. | 623/2.11 |
| 6,764,509 B2 | 7/2004 | Chinn et al. | 623/2.12 |
| 6,764,510 B2 | 7/2004 | Vidlund et al. | 623/2.34 |
| 6,767,362 B2 | 7/2004 | Schreck | 623/2.11 |
| 6,769,434 B2 | 8/2004 | Liddicoat et al. | 128/898 |
| 6,770,083 B2 | 8/2004 | Seguin | 606/142 |
| 6,780,200 B2 | 8/2004 | Jansen | 623/2.17 |
| 6,786,924 B2 | 9/2004 | Ryan et al. | 623/2.36 |
| 6,786,925 B1 | 9/2004 | Schoon et al. | 623/2.38 |
| 6,790,229 B1 | 9/2004 | Berreklouw | 623/2.1 |
| 6,790,230 B2 | 9/2004 | Beyersdorf et al. | 623/2.18 |
| 6,790,231 B2 | 9/2004 | Liddicoat et al. | 623/2.37 |
| 6,793,673 B2 | 9/2004 | Kowalsky et al. | 623/2.36 |
| 6,797,000 B2 | 9/2004 | Simpson et al. | 623/2.15 |
| 6,797,001 B2 | 9/2004 | Mathis et al. | 623/2.37 |
| 6,797,002 B2 | 9/2004 | Spence et al. | 623/2.38 |
| 6,802,860 B2 | 10/2004 | Cosgrove et al. | 623/2.11 |
| 6,805,710 B2 | 10/2004 | Bolling et al. | 623/2.36 |
| 6,805,711 B2 | 10/2004 | Quijano et al. | 623/2.37 |
| 6,810,882 B2 | 11/2004 | Langberg et al. | 128/898 |
| 6,821,297 B2 | 11/2004 | Snyders | 623/2.18 |
| 6,824,562 B2 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B2 | 1/2005 | Nguyen et al. | 623/2.13 |
| 6,840,246 B2 | 1/2005 | Downing | 128/898 |
| 6,840,957 B2 | 1/2005 | DiMatteo et al. | 623/1.24 |
| 6,846,324 B2 | 1/2005 | Stobie | 623/2.11 |
| 6,846,325 B2 | 1/2005 | Liddicoat | 623/2.4 |
| 6,858,039 B2 | 2/2005 | McCarthy | 623/2.36 |
| 6,869,444 B2 | 3/2005 | Gabbay | 623/2.36 |
| 6,872,226 B2 | 3/2005 | Cali et al. | 623/2.13 |
| 6,875,224 B2 | 4/2005 | Grimes | 606/219 |
| 6,875,230 B1 | 4/2005 | Morita et al. | 623/2.12 |
| 6,875,231 B2 | 4/2005 | Anduiza et al. | 623/2.14 |
| 6,881,199 B2 | 4/2005 | Wilk et al. | 604/9 |
| 6,881,224 B2 | 4/2005 | Kruse et al. | 623/2.11 |
| 6,883,522 B2 | 4/2005 | Spence et al. | 128/898 |
| 6,890,352 B1 | 5/2005 | Lentell | 623/2.27 |
| 6,890,353 B2 | 5/2005 | Cohn et al. | 623/2.37 |
| 6,893,459 B1 | 5/2005 | Macoviak | 623/2.11 |
| 6,893,460 B2 | 5/2005 | Spenser et al. | 623/2.14 |
| 6,896,700 B2 | 5/2005 | Lu et al. | 623/2.34 |
| 6,902,576 B2 | 6/2005 | Drasler et al. | 623/1.24 |
| 6,908,478 B2 | 6/2005 | Alferness et al. | 623/1.11 |
| 6,908,481 B2 | 6/2005 | Cribier | 623/2.11 |
| 6,911,043 B2 | 6/2005 | Myers et al. | 623/2.13 |
| 6,913,608 B2 | 7/2005 | Liddicoat et al. | 606/151 |
| 6,916,338 B2 | 7/2005 | Speziali | 623/2.12 |
| 6,918,917 B1 | 7/2005 | Nguyen et al. | 606/139 |
| 6,921,407 B2 | 7/2005 | Nguyen et al. | 606/142 |
| 6,921,811 B2 | 7/2005 | Zamora et al. | 536/21 |
| 6,926,715 B1 | 8/2005 | Hauck et al. | 606/41 |
| 6,926,730 B1 | 8/2005 | Nguyen et al. | 606/213 |
| 6,929,653 B2 | 8/2005 | Strecter | 606/200 |
| 6,932,838 B2 | 8/2005 | Schwartz et al. | 623/1.23 |
| 6,936,067 B2 | 8/2005 | Buchanan | 623/2.28 |
| 6,939,359 B2 | 9/2005 | Tu et al. | 606/159 |
| 6,942,694 B2 | 9/2005 | Liddicoat et al. | 623/2.36 |
| 6,945,957 B2 | 9/2005 | Freyman | 604/96.01 |
| 6,945,978 B1 | 9/2005 | Hyde | 606/142 |
| 6,945,996 B2 | 9/2005 | Sedransk | 623/2.12 |
| 6,945,997 B2 | 9/2005 | Huynh et al. | 623/2.17 |
| 6,949,122 B2 | 9/2005 | Adams et al. | 623/2.36 |
| 6,951,571 B1 | 10/2005 | Srivastava | 623/1.24 |
| 6,951,573 B1 | 10/2005 | Dilling | 623/2.2 |
| 6,953,332 B1 | 10/2005 | Kurk et al. | 425/275 |
| 6,955,689 B2 | 10/2005 | Ryan et al. | 623/2.36 |
| 6,958,076 B2 | 10/2005 | Acosta et al. | 623/1.24 |
| 6,962,605 B2 | 11/2005 | Cosgrove et al. | 623/2.36 |
| 6,964,682 B2 | 11/2005 | Nguyen-Thien-Nhon et al. | 623/2.11 |
| 6,964,683 B2 | 11/2005 | Kowalsky et al. | 623/2.36 |
| 6,964,684 B2 | 11/2005 | Ortiz et al. | 623/2.37 |
| 6,966,925 B2 | 11/2005 | Stobie | 623/2.11 |
| 6,966,926 B2 | 11/2005 | Mathis | 623/2.36 |

| Patent | Date | Inventor | Class |
|---|---|---|---|
| 6,974,464 B2 | 12/2005 | Quijano et al. | 606/108 |
| 6,974,474 B2 | 12/2005 | Pavcnik et al. | 623/1.24 |
| 6,974,476 B2 | 12/2005 | McGuckin, Jr. et al. | 623/2.36 |
| 6,976,995 B2 | 12/2005 | Mathis et al. | 623/2.37 |
| 6,979,350 B2 | 12/2005 | Moll et al. | 623/1.24 |
| 6,986,775 B2 | 1/2006 | Morales et al. | 606/139 |
| 6,989,027 B2 | 1/2006 | Allen et al. | 623/2.18 |
| 6,989,028 B2 | 1/2006 | Lashinski et al. | 623/2.37 |
| 6,997,950 B2 | 2/2006 | Chawla | 623/2.1 |
| 6,997,951 B2 | 2/2006 | Solem et al. | 623/2.37 |
| 7,004,176 B2 | 2/2006 | Lau | 128/898 |
| 7,007,396 B2 | 3/2006 | Rudko et al. | 33/512 |
| 7,011,669 B2 | 3/2006 | Kimblad | 606/151 |
| 7,011,681 B2 | 3/2006 | Vesely | 623/2.11 |
| 7,011,682 B2 | 3/2006 | Lashinski et al. | 623/2.37 |
| 7,018,406 B2 | 3/2006 | Seguin et al. | 623/2.1 |
| 7,018,407 B1 | 3/2006 | Wright et al. | 623/2.11 |
| 7,018,408 B2 | 3/2006 | Bailey et al. | 623/2.11 |
| 7,022,134 B1 | 4/2006 | Quijano et al. | 623/1.24 |
| 7,025,780 B2 | 4/2006 | Gabbay | 623/2.13 |
| 7,033,390 B2 | 4/2006 | Johnson et al. | 623/2.11 |
| 7,037,333 B2 | 5/2006 | Myers et al. | 623/2.13 |
| 7,037,334 B1 | 5/2006 | Hlavka et al. | 623/2.36 |
| 7,041,128 B2 | 5/2006 | McGuckin, Jr. et al. | 623/1.36 |
| 7,041,132 B2 | 5/2006 | Quijano et al. | 623/2.11 |
| 7,044,966 B2 | 5/2006 | Svanidze et al. | 623/2.1 |
| 7,044,967 B1 | 5/2006 | Solem et al. | 623/2.36 |
| 7,048,754 B2 | 5/2006 | Martin et al. | 606/232 |
| 7,048,757 B2 | 5/2006 | Shaknovich | 623/1.24 |
| 7,052,487 B2 | 5/2006 | Cohn et al. | 604/509 |
| 7,052,507 B2 | 5/2006 | Wakuda et al. | 606/194 |
| 7,063,722 B2 | 6/2006 | Marquez | 623/2.36 |
| 7,066,954 B2 | 6/2006 | Ryan et al. | 623/2.36 |
| 7,070,616 B2 | 7/2006 | Majercak et al. | 623/1.24 |
| 7,070,618 B2 | 7/2006 | Streeter | 623/2.36 |
| 7,077,862 B2 | 7/2006 | Vidlund et al. | 623/2.36 |
| 7,081,131 B2 | 7/2006 | Thornton | 623/1.24 |
| 7,087,064 B1 | 8/2006 | Hyde | 606/142 |
| 7,089,051 B2 | 8/2006 | Jäverud et al. | 600/547 |
| 7,090,695 B2 | 8/2006 | Solem et al. | 623/2.37 |
| 2001/0039450 A1* | 11/2001 | Pavcnik et al. | 623/1.24 |
| 2002/0013571 A1 | 1/2002 | Goldfarb et al. | 606/1 |
| 2002/0026216 A1 | 2/2002 | Grimes | 606/213 |
| 2002/0082630 A1 | 6/2002 | Menz et al. | 606/167 |
| 2002/0123802 A1 | 9/2002 | Snyders | 623/2.18 |
| 2002/0151970 A1 | 10/2002 | Garrison et al. | 623/2.11 |
| 2002/0169498 A1 | 11/2002 | Kim et al. | |
| 2002/0177894 A1* | 11/2002 | Acosta et al. | 623/1.24 |
| 2002/0183835 A1 | 12/2002 | Taylor et al. | 623/2.11 |
| 2002/0183838 A1 | 12/2002 | Liddicoat et al. | 623/2.11 |
| 2002/0198594 A1 | 12/2002 | Schreck | 623/2.11 |
| 2003/0050694 A1 | 3/2003 | Yang et al. | 623/2.11 |
| 2003/0130729 A1 | 7/2003 | Paniagua et al. | 623/2.11 |
| 2003/0149475 A1 | 8/2003 | Hyodoh et al. | |
| 2003/0163194 A1 | 8/2003 | Quijano et al. | 623/2.11 |
| 2003/0167071 A1 | 9/2003 | Martin et al. | 606/232 |
| 2003/0171806 A1 | 9/2003 | Mathis et al. | 623/2.36 |
| 2003/0199975 A1 | 10/2003 | Gabbay | 623/2.36 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0083045 A1 | 4/2004 | Nohara et al. | 623/2.13 |
| 2004/0087975 A1 | 5/2004 | Lucatero et al. | 606/139 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117004 A1 | 6/2004 | Osborne et al. | |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.13 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |
| 2004/0148020 A1 | 7/2004 | Vidlund et al. | 623/2.36 |
| 2004/0153052 A1 | 8/2004 | Mathis | 606/1 |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Kuehn et al. | 606/108 |

| Publication No. | Date | Inventor | Class |
|---|---|---|---|
| 2004/0167620 A1 | 8/2004 | Ortiz et al. | 623/2.11 |
| 2004/0172046 A1 | 9/2004 | Hlavka et al. | 606/142 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/108 |
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Lobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193191 A1 | 9/2004 | Starksen et al. | 606/153 |
| 2004/0193253 A1* | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/1.24 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | 623/2.17 |
| 2004/0210307 A1 | 10/2004 | Khairkhahan | 623/2.18 |
| 2004/0215333 A1 | 10/2004 | Duran et al. | 623/1.24 |
| 2004/0215339 A1 | 10/2004 | Drasler et al. | 623/3.1 |
| 2004/0220654 A1 | 11/2004 | Mathis et al. | 623/1.11 |
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1* | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |
| 2004/0236411 A1 | 11/2004 | Sarac et al. | 623/1.26 |
| 2004/0236418 A1 | 11/2004 | Stevens | 623/2.11 |
| 2004/0236419 A1 | 11/2004 | Milo | 623/2.36 |
| 2004/0243153 A1 | 12/2004 | Liddicoat et al. | 606/151 |
| 2004/0243219 A1 | 12/2004 | Fischer et al. | 623/1.15 |
| 2004/0243222 A1* | 12/2004 | Osborne et al. | 623/1.24 |
| 2004/0243227 A1 | 12/2004 | Starksen et al. | 623/2.11 |
| 2004/0243228 A1 | 12/2004 | Kowalsky et al. | 623/2.11 |
| 2004/0243230 A1 | 12/2004 | Navia et al. | 623/2.36 |
| 2004/0249452 A1 | 12/2004 | Adams et al. | 623/2.36 |
| 2004/0254600 A1 | 12/2004 | Zarbatany et al. | 606/194 |
| 2004/0254636 A1 | 12/2004 | Flagle et al. | 623/1.24 |
| 2004/0260276 A1 | 12/2004 | Rudko et al. | 606/15 |
| 2004/0260317 A1 | 12/2004 | Bloom et al. | 606/151 |
| 2004/0260322 A1* | 12/2004 | Rudko et al. | 606/167 |
| 2004/0260389 A1 | 12/2004 | Case et al. | 623/1.24 |
| 2004/0260390 A1 | 12/2004 | Sarac et al. | 623/1.24 |
| 2004/0260393 A1 | 12/2004 | Rahdert et al. | 623/2.36 |
| 2004/0260394 A1 | 12/2004 | Douk et al. | 623/2.36 |
| 2004/0267357 A1 | 12/2004 | Allen et al. | 623/2.11 |
| 2005/0004583 A1 | 1/2005 | Oz et al. | 606/142 |
| 2005/0004667 A1 | 1/2005 | Swinford et al. | 623/2.36 |
| 2005/0010285 A1 | 1/2005 | Lambrecht et al. | 623/2.18 |
| 2005/0010287 A1 | 1/2005 | Macoviak et al. | 623/2.36 |
| 2005/0015112 A1 | 1/2005 | Cohn et al. | 606/200 |
| 2005/0021056 A1 | 1/2005 | St. Goar et al. | 606/144 |
| 2005/0021136 A1 | 1/2005 | Xie et al. | 623/2.14 |
| 2005/0027261 A1 | 2/2005 | Weaver et al. | 604/246 |
| 2005/0027348 A1 | 2/2005 | Case et al. | 623/1.24 |
| 2005/0027351 A1 | 2/2005 | Reuter et al. | 623/2.11 |
| 2005/0027353 A1 | 2/2005 | Alferness et al. | 623/2.11 |
| 2005/0033398 A1 | 2/2005 | Seguin | 623/1.11 |
| 2005/0033419 A1 | 2/2005 | Alferness et al. | 623/2.11 |
| 2005/0033446 A1 | 2/2005 | Deem et al. | 623/23.6 |
| 2005/0038506 A1 | 2/2005 | Webler et al. | 623/2.11 |
| 2005/0038507 A1 | 2/2005 | Alferness et al. | 623/2.11 |
| 2005/0043790 A1 | 2/2005 | Seguin | 623/2.18 |
| 2005/0043792 A1 | 2/2005 | Solem et al. | 623/2.36 |
| 2005/0049679 A1 | 3/2005 | Taylor et al. | 623/1.15 |
| 2005/0049692 A1 | 3/2005 | Numamoto et al. | 623/1.24 |
| 2005/0049696 A1 | 3/2005 | Siess et al. | 623/2.11 |
| 2005/0049697 A1 | 3/2005 | Sievers | 623/2.26 |
| 2005/0054977 A1 | 3/2005 | Laird et al. | 604/96.01 |
| 2005/0055079 A1 | 3/2005 | Duran | 623/1.13 |
| 2005/0055087 A1 | 3/2005 | Starksen | 623/2.11 |
| 2005/0055088 A1 | 3/2005 | Liddicoat et al. | 623/2.11 |
| 2005/0055089 A1 | 3/2005 | Macoviak et al. | 623/2.37 |
| 2005/0060029 A1 | 3/2005 | Le et al. | 623/2.11 |
| 2005/0060030 A1 | 3/2005 | Lashinski et al. | 623/2.37 |
| 2005/0065460 A1 | 3/2005 | Laird | 604/20 |
| 2005/0065550 A1 | 3/2005 | Starksen et al. | 606/219 |
| 2005/0065594 A1 | 3/2005 | DiMatteo et al. | 623/1.24 |
| 2005/0065597 A1 | 3/2005 | Lansac | 623/2.11 |
| 2005/0070998 A1 | 3/2005 | Rourke et al. | 623/2.11 |
| 2005/0075584 A1 | 4/2005 | Cali | 600/587 |
| 2005/0075659 A1 | 4/2005 | Realyvasquez et al. | 606/167 |
| 2005/0075662 A1 | 4/2005 | Pedersen et al. | 606/194 |
| 2005/0075712 A1 | 4/2005 | Biancucci et al. | 623/1.11 |
| 2005/0075713 A1 | 4/2005 | Biancucci et al. | 623/1.11 |
| 2005/0075717 A1 | 4/2005 | Nguyen et al. | 623/1.26 |
| 2005/0075718 A1 | 4/2005 | Nguyen et al. | 623/1.26 |
| 2005/0075719 A1 | 4/2005 | Bergheim | 623/1.26 |
| 2005/0075720 A1 | 4/2005 | Nguyen et al. | 623/1.26 |
| 2005/0075723 A1 | 4/2005 | Schroeder et al. | 623/2.1 |
| 2005/0075724 A1 | 4/2005 | Svanidze et al. | 623/2.11 |
| 2005/0075725 A1 | 4/2005 | Rowe | 623/2.14 |
| 2005/0075726 A1 | 4/2005 | Svanidze et al. | 623/2.14 |
| 2005/0075728 A1 | 4/2005 | Nguyen et al. | 623/2.17 |
| 2005/0075729 A1 | 4/2005 | Nguyen et al. | 623/2.18 |
| 2005/0075730 A1 | 4/2005 | Myers et al. | 623/2.18 |
| 2005/0075731 A1 | 4/2005 | Artof et al. | 623/2.18 |
| 2005/0080483 A1 | 4/2005 | Solem et al. | 623/2.11 |
| 2005/0085900 A1 | 4/2005 | Case et al. | 623/1.24 |
| 2005/0085903 A1 | 4/2005 | Lau | 623/2.11 |
| 2005/0085904 A1 | 4/2005 | Lemmon | 623/2.11 |
| 2005/0090846 A1 | 4/2005 | Pedersen et al. | 606/159 |
| 2005/0096735 A1 | 5/2005 | Hojeibane et al. | 623/1.24 |
| 2005/0096738 A1 | 5/2005 | Cali et al. | 623/2.18 |
| 2005/0096739 A1 | 5/2005 | Cao | 623/2.19 |
| 2005/0096740 A1 | 5/2005 | Langberg et al. | 623/2.36 |
| 2005/0101975 A1 | 5/2005 | Nguyen et al. | 606/151 |
| 2005/0102026 A1 | 5/2005 | Turner et al. | 623/2.1 |
| 2005/0107810 A1 | 5/2005 | Morales et al. | 606/143 |
| 2005/0107811 A1 | 5/2005 | Starksen et al. | 606/143 |
| 2005/0107812 A1 | 5/2005 | Starksen et al. | 606/143 |
| 2005/0107872 A1 | 5/2005 | Mensah et al. | 623/2.14 |
| 2005/0113910 A1 | 5/2005 | Paniagua et al. | 623/2.14 |
| 2005/0119673 A1 | 6/2005 | Gordon et al. | 606/151 |
| 2005/0119734 A1 | 6/2005 | Spence et al. | 623/2.11 |
| 2005/0119735 A1 | 6/2005 | Spence et al. | 623/2.36 |
| 2005/0125011 A1 | 6/2005 | Spence et al. | 606/144 |
| 2005/0131438 A1 | 6/2005 | Cohn | 606/170 |
| 2005/0137449 A1 | 6/2005 | Nieminen et al. | 600/37 |
| 2005/0137450 A1 | 6/2005 | Aronson et al. | 600/37 |
| 2005/0137451 A1 | 6/2005 | Gordon et al. | 600/37 |
| 2005/0137676 A1* | 6/2005 | Richardson et al. | 623/1.11 |
| 2005/0137681 A1 | 6/2005 | Shoemaker et al. | 623/1.23 |
| 2005/0137682 A1 | 6/2005 | Justino | 623/1.24 |
| 2005/0137685 A1 | 6/2005 | Nieminen et al. | 623/2.11 |
| 2005/0137686 A1 | 6/2005 | Salahieh et al. | 623/2.11 |
| 2005/0137688 A1 | 6/2005 | Salahieh et al. | 623/2.11 |
| 2005/0137689 A1 | 6/2005 | Salahieh et al. | 623/2.11 |
| 2005/0137690 A1 | 6/2005 | Salahieh et al. | 623/2.11 |
| 2005/0137691 A1 | 6/2005 | Salahieh et al. | 623/2.11 |
| 2005/0137692 A1 | 6/2005 | Haug et al. | 623/2.11 |
| 2005/0137693 A1 | 6/2005 | Haug et al. | 623/2.11 |

| Publication No. | Date | Inventor | Class |
|---|---|---|---|
| 2005/0137694 A1 | 6/2005 | Haug et al. | 623/2.11 |
| 2005/0137696 A1 | 6/2005 | Salahieh et al. | 623/2.11 |
| 2005/0137697 A1 | 6/2005 | Salahieh et al. | 623/2.11 |
| 2005/0137698 A1 | 6/2005 | Salahieh et al. | 623/2.11 |
| 2005/0137699 A1 | 6/2005 | Salahieh et al. | 623/2.11 |
| 2005/0137700 A1 | 6/2005 | Spence et al. | 623/2.36 |
| 2005/0137701 A1 | 6/2005 | Salahieh et al. | 623/2.38 |
| 2005/0137702 A1 | 6/2005 | Haug et al. | 623/2.38 |
| 2005/0143807 A1 | 6/2005 | Pavcnik et al. | 623/1.24 |
| 2005/0143809 A1 | 6/2005 | Salahieh et al. | 623/2.11 |
| 2005/0143810 A1 | 6/2005 | Dauner et al. | 623/2.12 |
| 2005/0143811 A1 | 6/2005 | Realyvasquez | 623/2.36 |
| 2005/0149014 A1 | 7/2005 | Hauck et al. | 606/41 |
| 2005/0149179 A1 | 7/2005 | Mathis et al. | 623/2.11 |
| 2005/0149180 A1 | 7/2005 | Mathis et al. | 623/2.11 |
| 2005/0149181 A1 | 7/2005 | Eberhardt | 623/2.14 |
| 2005/0159810 A1 | 7/2005 | Filsoufi | 623/2.1 |
| 2005/0159811 A1 | 7/2005 | Lane | 623/2.14 |
| 2005/0165477 A1 | 7/2005 | Anduiza et al. | 623/2.11 |
| 2005/0165478 A1 | 7/2005 | Song | 623/2.22 |
| 2005/0171472 A1 | 8/2005 | Lutter | 604/101.03 |
| 2005/0171601 A1 | 8/2005 | Cosgrove et al. | 623/2.11 |
| 2005/0177227 A1 | 8/2005 | Heim et al. | 623/2.12 |
| 2005/0177228 A1 | 8/2005 | Solem et al. | 623/2.36 |
| 2005/0182483 A1 | 8/2005 | Osborne et al. | 623/1.24 |
| 2005/0184122 A1 | 8/2005 | Hlavka et al. | 227/175.1 |
| 2005/0187614 A1 | 8/2005 | Agnew | 623/1.24 |
| 2005/0187616 A1 | 8/2005 | Realyvasquez | 623/2.11 |
| 2005/0187617 A1 | 8/2005 | Navia | 623/2.13 |
| 2005/0192606 A1 | 9/2005 | Paul et al. | 606/159 |
| 2005/0192665 A1 | 9/2005 | Spenser et al. | 623/2.11 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0203549 A1 | 9/2005 | Realyvasquez | 606/142 |
| 2005/0203605 A1 | 9/2005 | Dolan | 623/1.11 |
| 2005/0203614 A1 | 9/2005 | Forster et al. | 623/2.11 |
| 2005/0203615 A1 | 9/2005 | Forster et al. | 623/2.11 |
| 2005/0203616 A1 | 9/2005 | Cribier | 623/2.11 |
| 2005/0203617 A1 | 9/2005 | Forster et al. | 623/2.14 |
| 2005/0203618 A1 | 9/2005 | Sharkawy et al. | 623/2.38 |
| 2005/0216039 A1 | 9/2005 | Lederman | 606/144 |
| 2005/0216077 A1 | 9/2005 | Mathis et al. | 623/2.11 |
| 2005/0216078 A1 | 9/2005 | Starksen et al. | 623/2.11 |
| 2005/0222675 A1 | 10/2005 | Sauter | 623/1.26 |
| 2005/0222678 A1 | 10/2005 | Lashinski et al. | 623/2.11 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |
| 2005/0234546 A1 | 10/2005 | Nugent et al. | 623/2.11 |
| 2005/0240200 A1 | 10/2005 | Bergheim | 606/108 |
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 11/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009804 A1 | 1/2006 | Pederson | 607/2 |
| 2006/0009841 A1 | 1/2006 | McGuckin et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Startksen et al. | 604/510 |
| 2006/0025784 A1 | 2/2006 | Startksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069429 A1 | 3/2006 | Spence et al. | 623/2.11 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.11 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |
| 2006/0116756 A1 | 6/2006 | Solem et al. | 623/2.11 |
| 2006/0122686 A1 | 6/2006 | Gilad et al. | 623/1.13 |
| 2006/0122692 A1 | 6/2006 | Gilad et al. | 623/1.24 |
| 2006/0122693 A1 | 6/2006 | Biadillah et al. | 623/1.24 |
| 2006/0127443 A1 | 6/2006 | Helmus | 424/423 |

| | | | | | |
|---|---|---|---|---|---|
| 2006/0129235 A1 | 6/2006 | Seguin et al. ............... 623/2.11 | WO | WO 2004/082537 | 9/2004 |
| 2006/0129236 A1 | 6/2006 | McCarthy .................. 623/2.36 | WO | WO 2004/082538 | 9/2004 |
| 2006/0135476 A1 | 6/2006 | Kutryk et al. ................. 514/59 | WO | WO 2004/082757 | 9/2004 |
| 2006/0135964 A1 | 6/2006 | Vesely ......................... 606/108 | WO | WO 2004/084746 | 10/2004 |
| 2006/0135967 A1 | 6/2006 | Realyvasquez ............. 606/142 | WO | WO 2004/084770 | 10/2004 |
| 2006/0136044 A1 | 6/2006 | Osborne et al. ............ 623/1.24 | WO | WO 2004/089246 | 10/2004 |
| 2006/0136045 A1 | 6/2006 | Flagle et al. ............... 623/1.24 | WO | WO 2004/089250 | 10/2004 |
| 2006/0136052 A1 | 6/2006 | Vesely ........................ 623/2.18 | WO | WO 2004/089253 | 10/2004 |
| 2006/0136054 A1 | 6/2006 | Berg et al. .................. 623/2.38 | WO | WO 2004/091449 | 10/2004 |
| 2006/0142846 A1 | 6/2006 | Pavcnik et al. ............. 623/1.24 | WO | WO 2004/091454 | 10/2004 |
| 2006/0142847 A1 | 6/2006 | Shaknovich ................ 623/1.24 | WO | WO 2004/093638 | 11/2004 |
| 2006/0142848 A1 | 6/2006 | Gabbay ....................... 623/1.26 | WO | WO 2004/093726 | 11/2004 |
| 2006/0142854 A1 | 6/2006 | Alferness et al. ........... 623/2.11 | WO | WO 2004/093728 | 11/2004 |
| 2006/0149358 A1 | 7/2006 | Zilla et al. .................. 623/1.22 | WO | WO 2004/093730 | 11/2004 |
| 2006/0149360 A1 | 7/2006 | Schwammenthal et al. ........................... 623/1.24 | WO | WO 2004/093745 | 11/2004 |
| | | | WO | WO 2004/093935 | 11/2004 |
| 2006/0149367 A1 | 7/2006 | Sieracki ...................... 623/2.21 | WO | WO 2004/096100 | 11/2004 |
| 2006/0149368 A1 | 7/2006 | Spence ....................... 623/2.37 | WO | WO 2004/103222 | 12/2004 |
| 2006/0161133 A1 | 7/2006 | Laird et al. .................. 604/509 | WO | WO 2004/103223 | 12/2004 |
| 2006/0161248 A1 | 7/2006 | Case et al. ..................... 623/2.1 | WO | WO 2004/105584 | 12/2004 |
| 2006/0161249 A1 | 7/2006 | Realyvasquez et al. .... 623/2.11 | WO | WO 2004/105651 | 12/2004 |
| 2006/0161250 A1 | 7/2006 | Shaw .......................... 623/2.17 | WO | WO 2004/112582 | 12/2004 |
| 2006/0167468 A1 | 7/2006 | Gabbay ....................... 606/108 | WO | WO 2004/112585 | 12/2004 |
| 2006/0167541 A1 | 7/2006 | Lattouf ....................... 623/2.11 | WO | WO 2004/112643 | 12/2004 |
| 2006/0167542 A1 | 7/2006 | Quintessenza .............. 623/2.12 | WO | WO 2004/112652 | 12/2004 |
| 2006/0167543 A1 | 7/2006 | Bailey et al. ................ 623/2.18 | WO | WO 2004/112657 | 12/2004 |
| | | | WO | WO 2004/112658 | 12/2004 |

FOREIGN PATENT DOCUMENTS

| | | |
|---|---|---|
| EP | 0 466 518 | 1/1992 |
| FR | 2 728 457 | 6/1996 |
| WO | WO 88/00459 | 1/1988 |
| WO | WO 90/15582 | 12/1990 |
| WO | WO 95/01669 | 1/1995 |
| WO | WO 96/19159 | 6/1996 |
| WO | WO 98/03656 | 1/1998 |
| WO | WO 98/46115 | 10/1998 |
| WO | WO 99/04724 | 2/1999 |
| WO | WO 00/67679 | 11/2000 |
| WO | WO 01/15650 | 3/2001 |
| WO | WO 01/17462 | 3/2001 |
| WO | WO 03/047468 | 6/2003 |
| WO | WO 03/084443 | 10/2003 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/047677 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |
| WO | WO 2004/075789 | 9/2004 |
| WO | WO 2004/080352 | 9/2004 |
| WO | WO 2004/082523 | 9/2004 |
| WO | WO 2004/082527 | 9/2004 |
| WO | WO 2004/082528 | 9/2004 |
| WO | WO 2004/082536 | 9/2004 |
| WO | WO 2005/000152 | 1/2005 |
| WO | WO 2005/002424 | 1/2005 |
| WO | WO 2005/002466 | 1/2005 |
| WO | WO 2005/004753 | 1/2005 |
| WO | WO 2005/007017 | 1/2005 |
| WO | WO 2005/007018 | 1/2005 |
| WO | WO 2005/007036 | 1/2005 |
| WO | WO 2005/007037 | 1/2005 |
| WO | WO 2005/009285 | 2/2005 |
| WO | WO 2005/009286 | 2/2005 |
| WO | WO 2005/009505 | 2/2005 |
| WO | WO 2005/009506 | 2/2005 |
| WO | WO 2005/011473 | 2/2005 |
| WO | WO 2005/011534 | 2/2005 |
| WO | WO 2005/011535 | 2/2005 |
| WO | WO 2005/013860 | 2/2005 |
| WO | WO 2005/018507 | 3/2005 |
| WO | WO 2005/021063 | 3/2005 |
| WO | WO 2005/023155 | 3/2005 |
| WO | WO 2005/025644 | 3/2005 |
| WO | WO 2005/027790 | 3/2005 |
| WO | WO 2005/027797 | 3/2005 |
| WO | WO 2005/034812 | 4/2005 |
| WO | WO 2005/039428 | 5/2005 |
| WO | WO 2005/039452 | 5/2005 |
| WO | WO 2005/046488 | 5/2005 |
| WO | WO 2005/046528 | 5/2005 |
| WO | WO 2005/046529 | 5/2005 |
| WO | WO 2005/046530 | 5/2005 |
| WO | WO 2005/046531 | 5/2005 |
| WO | WO 2005/048883 | 6/2005 |
| WO | WO 2005/049103 | 6/2005 |
| WO | WO 2005/051226 | 6/2005 |
| WO | WO 2005/055811 | 6/2005 |
| WO | WO 2005/055883 | 6/2005 |
| WO | WO 2005/058206 | 6/2005 |
| WO | WO 2005/065585 | 7/2005 |
| WO | WO 2005/065593 | 7/2005 |
| WO | WO 2005/065594 | 7/2005 |
| WO | WO 2005/070342 | 8/2005 |
| WO | WO 2005/070343 | 8/2005 |
| WO | WO 2005/072654 | 8/2005 |
| WO | WO 2005/072655 | 8/2005 |
| WO | WO 2005/079706 | 9/2005 |
| WO | WO 2005/082288 | 9/2005 |
| WO | WO 2005/082289 | 9/2005 |

| | | | | | | |
|---|---|---|---|---|---|---|
| WO | WO 2005/084595 | 9/2005 | | WO | WO 2006/034245 | 3/2006 |
| WO | WO 2005/087139 | 9/2005 | | WO | WO 2006/035415 | 4/2006 |
| WO | WO 2005/087140 | 9/2005 | | WO | WO 2006/041505 | 4/2006 |
| WO | WO 2006/000763 | 1/2006 | | WO | WO 2006/044679 | 4/2006 |
| WO | WO 2006/000776 | 1/2006 | | WO | WO 2006/048664 | 5/2006 |
| WO | WO 2006/002492 | 1/2006 | | WO | WO 2006/050459 | 5/2006 |
| WO | WO 2006/004679 | 1/2006 | | WO | WO 2006/050460 | 5/2006 |
| WO | WO 2006/005015 | 1/2006 | | WO | WO 2006/054107 | 5/2006 |
| WO | WO 2006/009690 | 1/2006 | | WO | WO 2006/054930 | 5/2006 |
| WO | WO 2006/011127 | 2/2006 | | WO | WO 2006/055982 | 5/2006 |
| WO | WO 2006/012011 | 2/2006 | | WO | WO 2006/060546 | 6/2006 |
| WO | WO 2006/012013 | 2/2006 | | WO | WO 2006/063108 | 6/2006 |
| WO | WO 2006/012038 | 2/2006 | | WO | WO 2006/063181 | 6/2006 |
| WO | WO 2006/012068 | 2/2006 | | WO | WO 2006/063199 | 6/2006 |
| WO | WO 2006/012322 | 2/2006 | | WO | WO 2006/064490 | 6/2006 |
| WO | WO 2006/019498 | 2/2006 | | WO | WO 2006/065212 | 6/2006 |
| WO | WO 2006/026371 | 3/2006 | | WO | WO 2006/065930 | 6/2006 |
| WO | WO 2006/026377 | 3/2006 | | WO | WO 2006/066148 | 6/2006 |
| WO | WO 2006/026912 | 3/2006 | | WO | WO 2006/066150 | 6/2006 |
| WO | WO 2006/027499 | 3/2006 | | WO | WO 2006/069094 | 6/2006 |
| WO | WO 2006/028821 | 3/2006 | | WO | WO 2006/070372 | 7/2006 |
| WO | WO 2006/029062 | 3/2006 | | WO | WO 2006/073628 | 7/2006 |
| WO | WO 2006/031436 | 3/2006 | | WO | WO 2006/076890 | 7/2006 |
| WO | WO 2006/031469 | 3/2006 | | | | |
| WO | WO 2006/032051 | 3/2006 | | * cited by examiner | | |

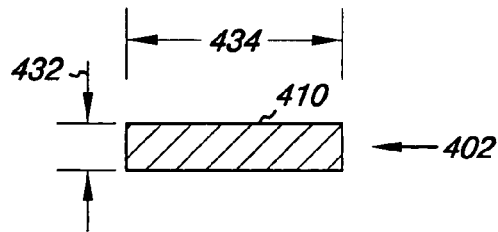
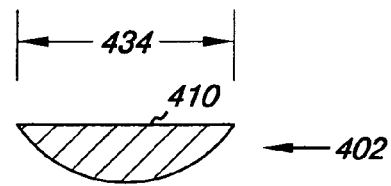
*Fig. 4A*  *Fig. 4B*
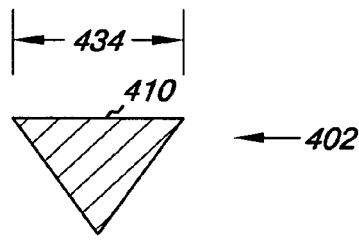
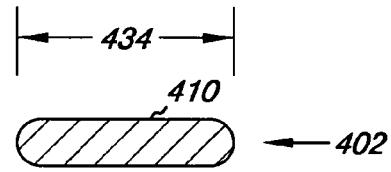
*Fig. 4C*  *Fig. 4D*
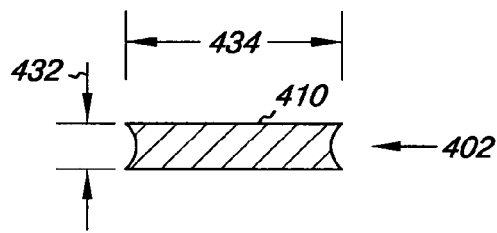
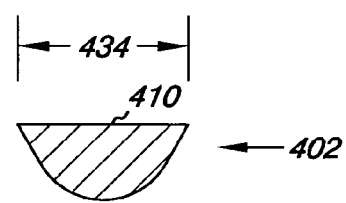
*Fig. 4E*  *Fig. 4F*
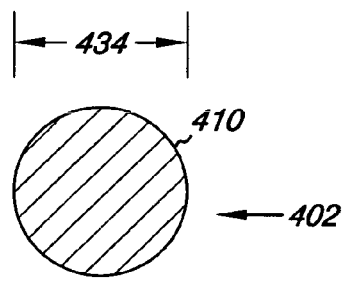
*Fig. 4G*

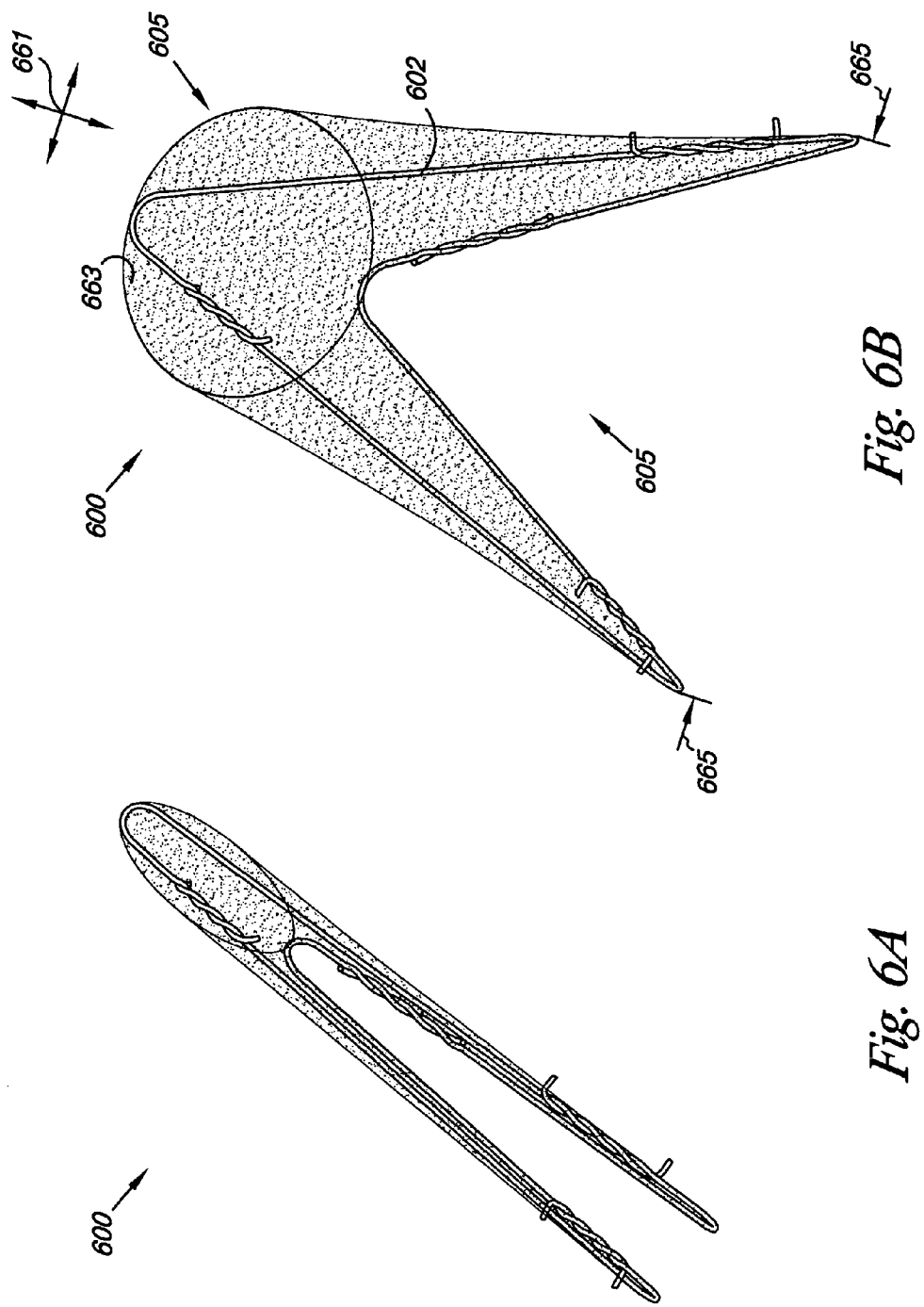

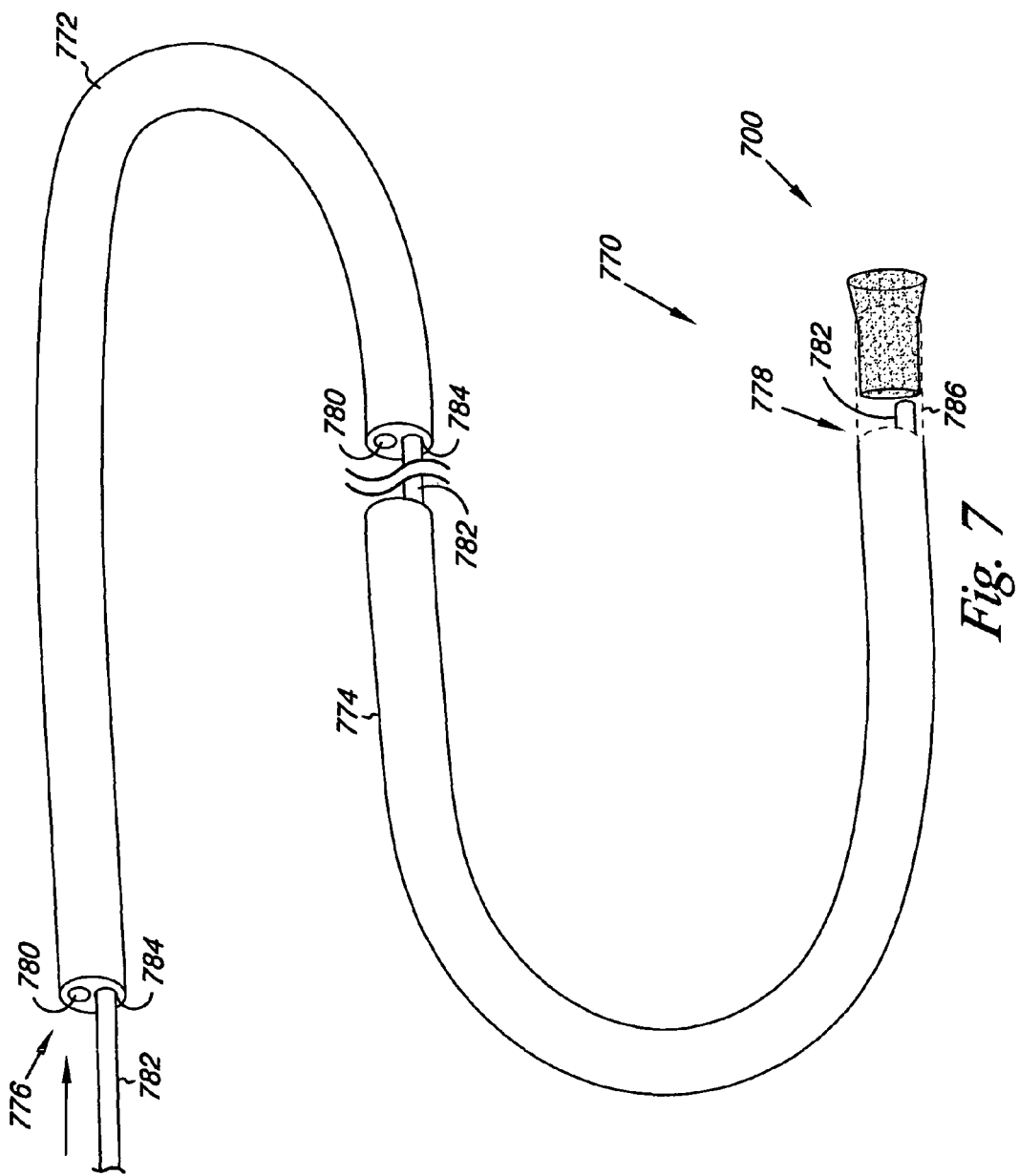

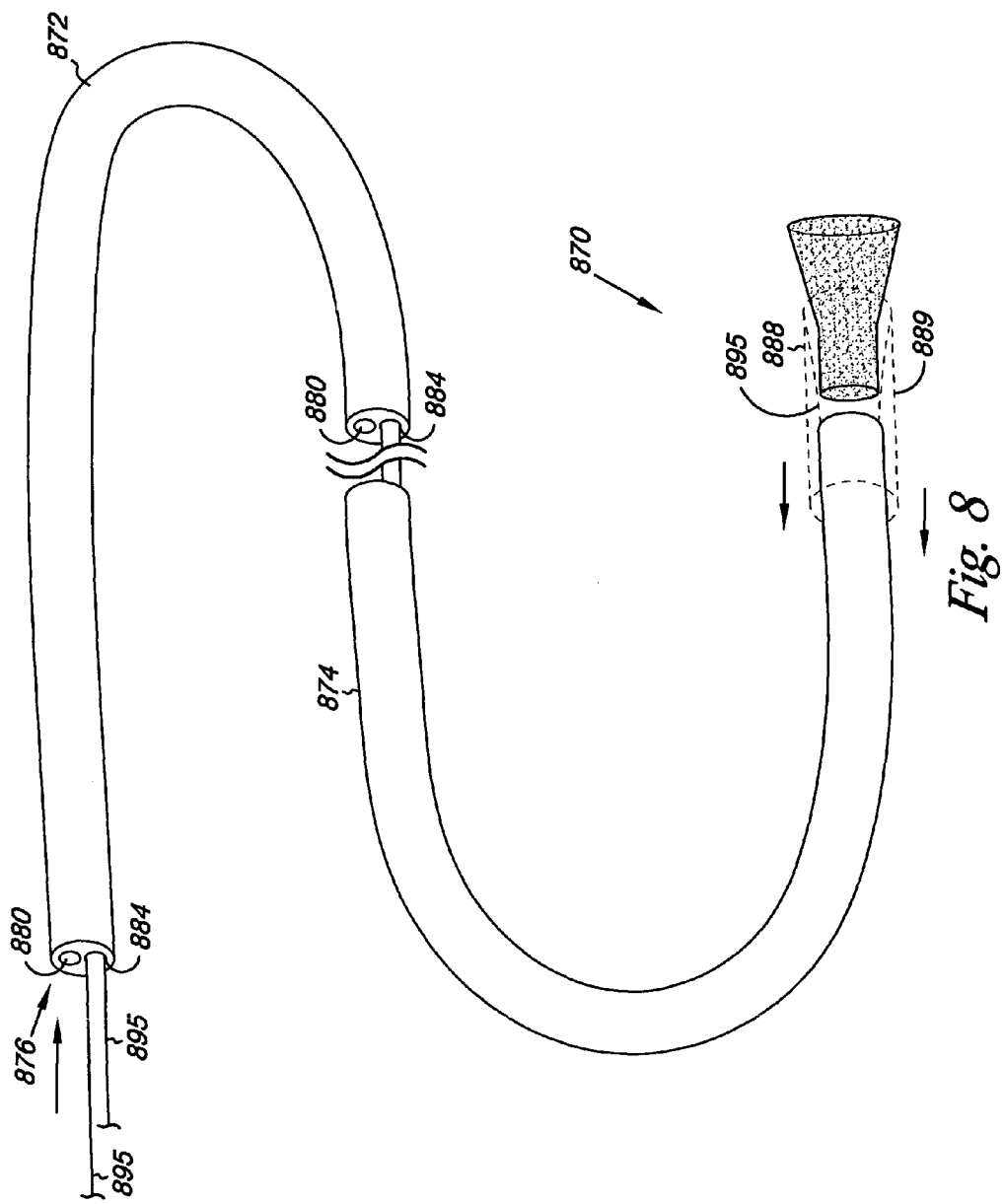

VENOUS VALVE APPARATUS, SYSTEM, AND METHOD

FIELD OF THE INVENTION

The present invention relates generally to apparatus, systems, and methods for use in a lumen; and more particularly to venous valve apparatus, systems, and methods for use in the vasculature system.

BACKGROUND OF THE INVENTION

The venous system of the legs uses valves and muscles as part of the body's pumping mechanism to return blood to the heart. Venous valves create one way flow to prevent blood from flowing away from the heart. When valves fail, blood can pool in the lower legs resulting in swelling and ulcers of the leg. The absence of functioning venous valves can lead to chronic venous insufficiency.

Techniques for both repairing and replacing the valves exist, but are tedious and require invasive surgical procedures. Direct and indirect valvuoplasty procedures are used to repair damaged valves. Transposition and transplantation are used to replace an incompetent valve. Transposition involves moving a vein with an incompetent valve to a site with a competent valve. Transplantation replaces an incompetent valve with a harvested valve from another venous site. Prosthetic valves can be transplanted into the venous system, but current devices are not successful enough to see widespread usage.

BRIEF DESCRIPTION OF THE DRAWINGS

FIGS. 4A-4G illustrate embodiments of cross-sectional geometries for use with embodiments of a valve.

FIGS. 6A-6B illustrate a valve in an expanded and a collapsed state.

FIG. 7 illustrates an embodiment of a system that includes a valve.

FIG. 8 illustrates an embodiment of a system that includes a valve.

DETAILED DESCRIPTION

Figure 1A:
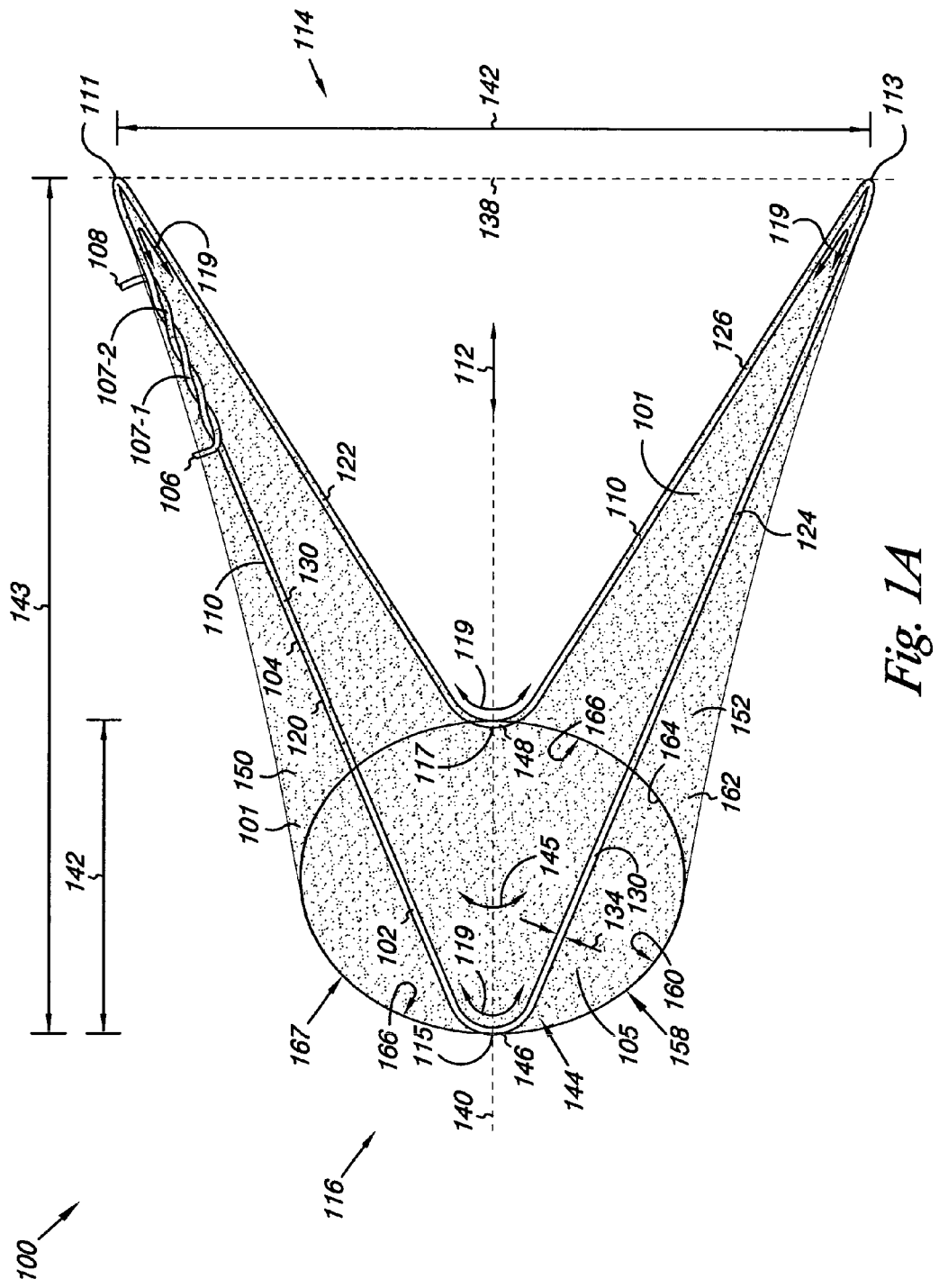
FIGS. 1A-1B illustrate an embodiment of a valve.

Embodiments of the present invention are directed to an apparatus, system, and method for valve replacement or augmentation. For example, the apparatus can include a valve that can be used to replace or augment an incompetent valve in a body lumen. Embodiments of the valve can include a frame and cover that can be implanted through minimally-invasive techniques into the body lumen. In one example, embodiments of the apparatus, system, and method for valve replacement or augmentation may help to maintain antegrade blood flow, while decreasing retrograde blood flow in a venous system of individuals having venous insufficiency, such as venous insufficiency in the legs.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of the valve according to the present invention. In addition, discussion of features and/or attributes for an element with respect to one Fig. can also apply to the element shown in one or more additional Figs.

FIGS. 1A-1B, 2A-2B, and 3 provide illustrations of various embodiments of a valve of the present invention. Generally, the valve can be implanted within the fluid passageway of a body lumen, such as for replacement or augmentation of a valve structure within the body lumen (e.g., a venous valve). In one embodiment, the valve of the present invention may be beneficial to regulate the flow of a bodily fluid through the body lumen in a single direction.

FIG. 1A illustrates one embodiment of a venous valve 100. Venous valve 100 includes a frame 102 and a cover 101, where both the frame 102 and the cover 101 can resiliently collapse and expand, as will be discussed herein. The frame 102 and the cover 101 can define a lumen 105 of the valve 100. Lumen 105 allows for, among other things, fluid to move through the valve 100. The frame 102 can be expanded to provide the lumen (e.g., 105 in FIGS. 1A-1B, 205 in FIG. 2A, and 305 in FIG. 3) having a number of sizes. For example, the size of the lumen can be determined based upon the type of body lumen and the body lumen size in which the valve is to be placed.

The frame 102 can include one or more elongate members 104. The elongate member 104 can include a first member end 106 and a second member end 108. The frame 102 illustrated in FIG. 1A includes a single elongate member 104. However, in various embodiments, the frame 102 can have a plurality of elongate members. For example, in FIG. 2A, the frame includes four (4) elongate members 204-1 through 204-4, and in FIG. 3, the frame includes eight (8) elongate members 304-1 through 304-8.

The first and second member ends 106 and 108 of the elongate member 104 can extend radially from an outer surface 110 of the frame 102 relative a central longitudinal axis 112. In one embodiment, the radial extensions of the first and second member ends 106 and 108 can function to engage and attach to a body lumen, e.g., a vein, for securing the frame 102 within a body lumen as will be discussed herein. In addition, the first and second member ends 106 and 108 can extend parallel to the elongate member 104. In such embodiments, the first and second member ends 106 and 108 can be positioned adjacent to and parallel to the elongate member 104 of the frame 102 such that the first and second member ends 106 and 108 point toward the vertices of the frame.

In the various embodiments of the present invention, the first and second member ends 106 and 108 can extend radially from the outer surface as illustrated in FIG. 1A, and/or they can extend adjacent to and parallel to the elongate member 104 of the frame 102. In some embodiments, the first and second member ends 106 and 108 can include anchoring elements, e.g., barbs, for engaging and attaching to a body lumen as will be discussed herein.

The elongate member 104 further includes a predetermined portion 107-1 and 107-2 adjacent the first and second member ends 106 and 108. As used herein, the predetermined portion 107-1 and 107-2 includes a section of the elongate member 104 adjacent the first member end 106 and the second member end 108 that can be used to engage each other thereby forming a closed circumference of the frame 102. For example, as illustrated in FIG. 1A, the predetermined portion 107-1 adjacent the first member end 106 and the predetermined portion 107-2 adjacent the second member end 108 entwine to form a closed circumference of the frame 102.

The entwined predetermined portions 107-1 and 107-2 can include a number of twists having a range of twists from 1 twist(s) to 4 twists. As used herein, a twist can include a predetermined portion rotated once around another predetermined portion. For example, in the embodiment shown in FIG. 1A, the predetermined portion 107-1 includes two rotations around predetermined portion 107-2 and predetermined portion 107-2 includes two rotations around predetermined portion 107-1. Thus, in this embodiment, the predetermined portions 107-1 and 107-2 entwine to include two twists each to form the closed circumference of the frame 102. As will be appreciated, fractional values for a twist are possible (e.g., 1.5 twists) along with twist values less than 1 twists and greater than 4 twists.

The frame 102 can further be configured to include vertices relative a first end 114 and a second end 116 of the frame 102. The frame 102 can include a series of bends to provide the vertices relative the first and the second ends 114 and 116 of the frame 102. For example, the frame 102 can include four corner portions 119 having bends that include a first vertex 111, a second vertex 113, a third vertex 115, and a fourth vertex 117. The corner portions 119 of the frame 102 provide the first vertex 111 and the second vertex 113 relative the second end 116 of the frame 102. The corner portions 119 also provide the third vertex 115 and the fourth vertex 117 at the second end 116 relative the first and second vertices 111 and 113. In one embodiment, the first vertex 111 and the second vertex 113 are positioned opposite each other along a first common axis 138 at the first end 114 of the frame 102. Similarly, the third vertex 115 and the fourth vertex 117 are positioned opposite each other along a second common axis 140. Other relative positions for the vertices 111, 113, 115, and 117 are also possible.

In the various embodiments described herein, the corner portions 119 of the frame 102 can provide a spring force against radial compression of the frame 102. The corner portions 119 can further provide elastic regions for the frame 102. Typically, these elastic regions occur at bent portions, i.e., corner portions 119, of the frame 102 forming the vertices. In one embodiment, the elastic regions allow the valve 100 to accommodate changes in body lumen size (e.g., diameter of the body lumen) by flexing to expand and/or contracting to change the radial shape of the frame 102. In one embodiment, the corner portions 119 of the frame 102 can act as springs to allow the valve 100 to resiliently radially collapse and expand. The frame 102 can also provide sufficient contact and expansion force with the surface of a body lumen wall to encourage fixation of the valve 100 and to prevent retrograde flow within the body lumen around the edges of the frame 102 and the surface of a lumen when combined with a closed state of the valve leaflets (described in more detail below) attached thereto.

The frame 102 can further include elongate portions 120, 122, 124, and 126. As used herein, an elongate portion includes a portion of the frame 102 that extends between the vertices of the frame 102. For example, as illustrated in FIG. 1A, a first elongate portion 120 can extend from approximately the first vertex 111 to approximately the second vertex 115. Similarly, a second elongate portion 122 can extend from approximately the first vertex 111 to approximately the fourth vertex 117. Thus, in various embodiments, an elongate portion can include at least one elongate member 104, and possibly predetermined portion 107-1 and 107-2 including the first and a second member ends 106 and 108.

Figure 1B:
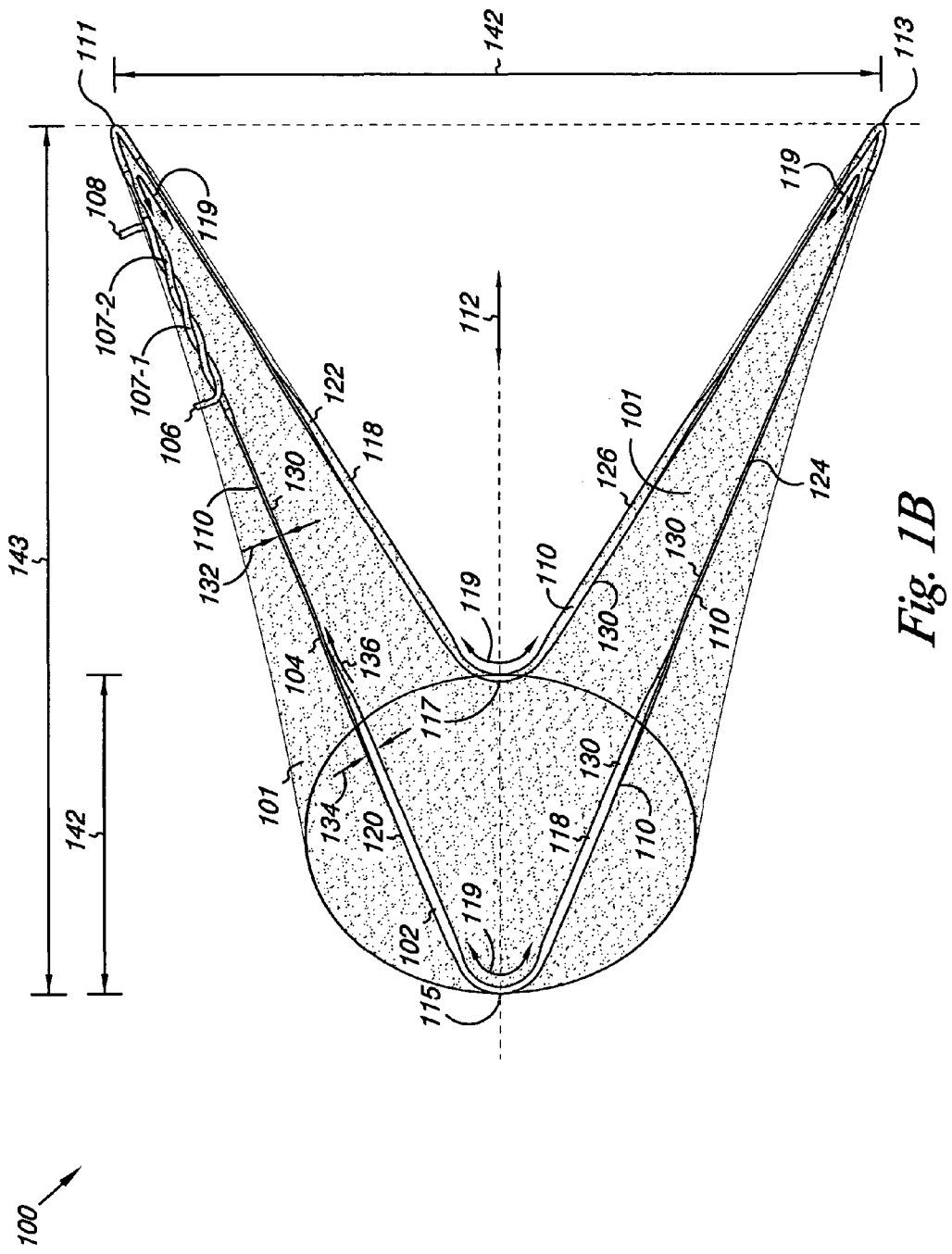

As illustrated in FIGS. 1A and 1B, the frame 102 can have similar and/or different cross-sectional geometries along its length. The similarity and/or the differences in the cross-sectional geometries can be based on one or more desired functions to be elicited from each portion of the frame 102 (e.g., the elongate portion 120, 122, 124, 126, and the vertices 111, 113, 115 and 117). For example, FIG. 1A provides an illustration of the similar cross-sectional geometry, where the frame 102 includes a circular cross-section along the length of the frame including the predetermined portion 107-1 and 107-2, and the first and second member ends 106 and 108 respectively.

Alternatively, FIG. 1B provides an illustration of the varying cross-sectional geometry. In FIG. 1B, the frame 102 can include a strip 118 having a rectangular cross-section along the elongate portions 120, 122, 124, and 126 of the frame 102. In this embodiment, the elongate portions 120, 122, 124, and 126 each include a planar inner surface 130 and a planar outer surface 110 with the other portions of the frame 102 surfaces having a non-planar configuration. That is, the predetermined portion 107-1 and 107-2, and the corner portions 119 including the vertices 111, 113, 115, and 117 of the frame 102, can have one or more of a round (e.g., circular, oval, and/or elliptical) cross-sectional geometry, while the elongate portions 120, 122, 124, and 126 can have a rectangular cross-sectional geometry.

As shown in FIG. 1B, the corner portions 119 of the vertices 111, 113, 115, and 117 have a circular cross-sectional geometry. As will be appreciated however, each of the corner portions 119 of the frame 102 can themselves have similar and/or different cross-sectional geometries (e.g., corner portions 119 of vertices 111 and 113 could have a circular cross-sectional geometry, while the corner portions 119 of vertices 115 and 117 could have an elliptical cross-sectional geometry). Other combinations of cross-sectional geometries are possible.

In the embodiment of FIG. 1B, the strip 118 of material forming the elongate portions 120, 122, 124, and 126 of the frame 102 can include a dimension of height 132 and width 134 between the inner surface 130 and the outer surface 110 so as to provide an aspect ratio of the width 134 to the height 132. As will be appreciated, the aspect ratio can have one or more values that provide the frame 102 with sufficient strength, flexibility and/or rigidity for the environment, including the physical demands, in which the venous valve 100 is to be used Embodiments of the invention are not so limited.

In addition, the cross-sectional geometries can include varying dimensions along the length of the valve 100. For example, in the embodiment shown in FIG. 2B, illustrated as a section of the frame 202, the cross-sectional diameter 247 of the predetermined portion 207-1 and 207-2 is the same as the cross-sectional diameter 246 of the elongate members 204-1 and 204-2. In this embodiment, each predetermined portion 207-1 and 207-2 has a cross-sectional diameter half the size of the cross-sectional diameter of the elongate members 204-1 and 204-2. As a result of the predetermined portion 207-1 and 207-2 being entwined, the closed circumference of the frame 202 has a single uniform diameter along its length. That is, the diameters 246 of the elongate members 204-1 and 204-2 equal the diameter 247 of the entwined predetermined portion 207-1 and 207-2.

While the elongate portions 120, 122, 124, and 126 are illustrated herein as having a circular and planar cross-sectional configuration as shown in FIGS. 1A and 1B, other configurations are also possible. For example, FIGS. 4A-4G provide non-limiting examples of cross-sectional geometries for the elongate member 104 (e.g., elongate portions 120, 122, 124, and 126) of the frame 102. As shown in FIGS. 4A-4G, examples of cross-sectional geometries include, but are not limited to, rectangular geometries having perpendicular sides (FIG. 4A), one or more convex sides (FIG. 4D), and one or more concave sides (FIG. 4E), semi-circular (FIGS. 4B and 4F), circular (FIG. 4G) and triangular (FIG. 4C).

As will be appreciated, the dimensions of the cross-sectional geometries of the different parts of the frame 102, e.g., the first and second member ends 106 and 108, the predetermined portion 107-1 and 107-2, and the one or more elongate members 104 can each be determined based upon the location into which the valve 100 is to be implanted in the patient. Thus, in the various embodiments of the present invention, the various parts of the frame can each include a cross-sectional geometry having various widths 134, and heights 132. For example, the elongate portions 120, 122, 124, and 126, as seen in FIG. 1B, can each include the cross-sectional geometry shown in FIG. 4A and the corner portions 119 can each include the circular geometry, such as the cross-sectional geometry shown in FIG. 4G. Other combinations of cross-sectional geometries are also possible.

Additional examples of cross-sectional geometries for one or more portions of the frame 102 include, but are not limited to, tubular, I-shaped, T-shaped, oval, and trapezoidal. These embodiments, however, are not limited to the present examples as other cross-sectional geometries are also possible. As such, the present invention should not be limited to the illustration of the frame in FIGS. 1A-1B, 2A-2B and 3.

In addition to cross-sectional geometries for the one or more portions of the frame 102, the frame can exhibit partial helical twisting. For example, the frame 102 in FIG. 1B can further include at least a partial helical configuration 136 in the elongate portions 120, 122, 124, and 126. The elongate portion 120 of frame 102 can follow the partial helical configuration 136 extending along the longitudinal central axis 112 of the frame 102 such that elongate portions 120, 122, 124, and 126 of the frame 102 maintain a planar relationship with the walls of a body lumen. In other words, the helical twisting 136 of the frame 102 allows the planar outer surface 110 of the elongate portions 120, 122, 124, and 126 of the frame 102 to contact the wall of a body lumen in a patient.

In the various embodiments, the frame 102 can provide symmetrical relationships for the one or more elongate portions 120, 122, 124, and 126 and the vertices 111, 113, 115, and 117. For example, as illustrated in FIGS. 1A-1B, 2A, and 3, the frame 102 can provide bilateral and radial symmetries, among other things. With respect to bilateral symmetry, in FIG. 1A, the second elongate portion 122 and the fourth elongate portion 126 can have a symmetrical relationship to the first elongate portion 120 and the third elongate portion 124, respectively, across a plane extending from the first common axis 138 and bisecting the second common axis 140 perpendicularly. In other words, the second elongate portion 122 and the fourth elongate portion 126 can provide a mirror image of the first elongate portion 120 and the third elongate portion 124, respectively. Similarly, the first vertex 111 and the third vertex 115 can provide mirror images of the second vertex 113 and the fourth vertex 117, respectively.

As will be appreciated, the various members and vertices of the frame 102 need not necessarily, however, display a symmetrical relationship in order to practice the embodiments of the present invention. For example, in the embodiments illustrated in FIGS. 1A and 1B, the radial relationship of the first elongate portion 120 and the second elongate portion 122 can be set apart approximately ninety (90) degrees or greater relative each other around the longitudinal central axis 112 of the frame 102. In which case the first elongate portion 120 and the fourth elongate portion 122, and the second elongate portion 122 and the third elongate portion 124 can be set apart approximately ninety (90) degrees or less relative each other around the longitudinal central axis 112 of the frame 102. Other radial relationships are also possible.

Referring again to FIG. 1A, the outer diameter 142 and a length 143 of valve 100 can have a number of values. As used herein, the outer diameter can include the distance between two vertices located at the same common axis. For example, the outer diameter 142 can include the distance between the first vertex 111 and the second vertex 113, which are positioned at the first common axis 138. In addition, the length 143 can be defined as the distance between a vertex on the first common axis and a vertex on the second common axis. For example, the length 143 of the valve 100 can include the distance between the first vertex 111, which is positioned at the first common axis 138, and the third vertex 115, which is positioned at the second common axis 140. As will be appreciated, the outer diameter 142 and the length 143 of valve 100 can each be determined based upon the location into which the valve 100 is to be implanted.

The embodiments of the frame 102 can also be constructed of one or more of a number of materials and in a variety of configurations. Generally, the frame 102 can have a closed circumference along its length. The frame can also be self-expanding. Examples of self-expanding frames include those formed from temperature-sensitive memory alloy such as those sold under the trade designator Nitinol, which can change shape at a designated temperature or temperature range. The self-expanding frames can also include those having a spring-bias. In addition, the frame 102 can have a configuration that allows the valve 100 embodiments to be radially expandable through the use of a balloon catheter.

As will be appreciated, in various embodiments, additional spring force can be imparted to the frame 102 from the compression of the partial helical configuration 136 of the frame 102 illustrated in FIG. 1B. For example, as all or a portion of the frame 102 is radially compressed towards longitudinal central axis 112, both the corner portions 119 and the partial helical configuration 136 of the frame 102 can resiliently bend (e.g., the spiral shape of the partial helical configuration is turned more tightly) to store elastic force (e.g., elastic potential energy) that allows the frame 102 to expand radially so as to return towards its uncompressed state.

The materials used in constructing frame 102 can also be pre- and/or post-treated. For example, the material characteristics of the frame can be modified by imparting to the corner portions, e.g. 119, 219, and 319, a radial arc that flares the frame outward from the longitudinal central axis. In one embodiment, the radial arc may be sufficiently large such that portions of the frame at the corners may extend beyond the outer diameter of the frame as defined by the first planar surface. Illustrations of such a radial arc, such as those described herein, can be found in co-pending U.S. patent application Ser. No. 11/150,331, filed on Jun. 10, 2005 and entitled "Venous Valve System, and Method", which is incorporated herein by reference in its entirety.

As discussed above, the embodiments of the frame can also be formed from one or more elongate members 104. For example, the frame 102 shown in FIGS. 1A and 1B include a single elongate member 104. In one embodiment, the single elongate member 104 can be bent around an elongate tubular mandrel to form the frame 102. The predetermined portion 107-1 and 107-2 of the elongate member 104 can be entwined to form the closed circumference of the frame and the first and second member ends 106 and 108 of the elongate member 104 can be bent perpendicularly relative to the elongate member 104 to extend radially from the outer surface 110 of the frame 102. In an alternative embodiment, methods of joining the elongate member to create the elastic region can further include, but are not limited to, welding, gluing, and fusing the frame member. The frame can also be heat set by methods known for the material(s) which forms the frame.

The frame 102 can be formed from a number of materials. For example, the frame can be formed from a biocompatible metal, metal alloy, polymeric material, or combination thereof. As discussed herein, the frame can be self-expanding or balloon expandable. In addition, the frame can be configured so as to have the ability to move radially between the collapsed state and the expanded state. To accomplish this, the material used to form the frame should exhibit an elastic modulus and a yield stress for large elastic strains that can recover from elastic deformations. Examples of suitable materials include, but are not limited to, medical grade stainless steel (e.g., 316L), titanium, tantalum, platinum alloys, niobium alloys, cobalt alloys, alginate, or combinations thereof. Additional frame embodiments may be formed from a shape-memory material, such as shape memory plastics, polymers, and thermoplastic materials which are inert in the body. Shaped memory alloys having superelastic properties generally made from ratios of nickel and titanium, commonly known as Nitinol, are also possible materials. Other materials are also possible.

As discussed herein, in various embodiments, the frame 102 can further include one or more anchoring elements. For example, the one or more anchoring elements can include, but are not limited to, the first and second member ends 106 and 108, one or more barbs projecting obliquely from the first and second member ends 106 and 108 of the frame 102, and/or from the one or more elongate members 104 of the frame 102. The valve 100 can further include one or more radiopaque markers (e.g., tabs, sleeves, welds). For example, one or more portions of the frame 102 can be formed from a radiopaque material. Radiopaque markers can be attached to and/or coated onto one or more locations along the frame. Examples of radiopaque material include, but are not limited to, gold, tantalum, and platinum. The position of the one or more radiopaque markers can be selected so as to provide information on the position, location and orientation of the valve during its implantation.

Figure 2A:
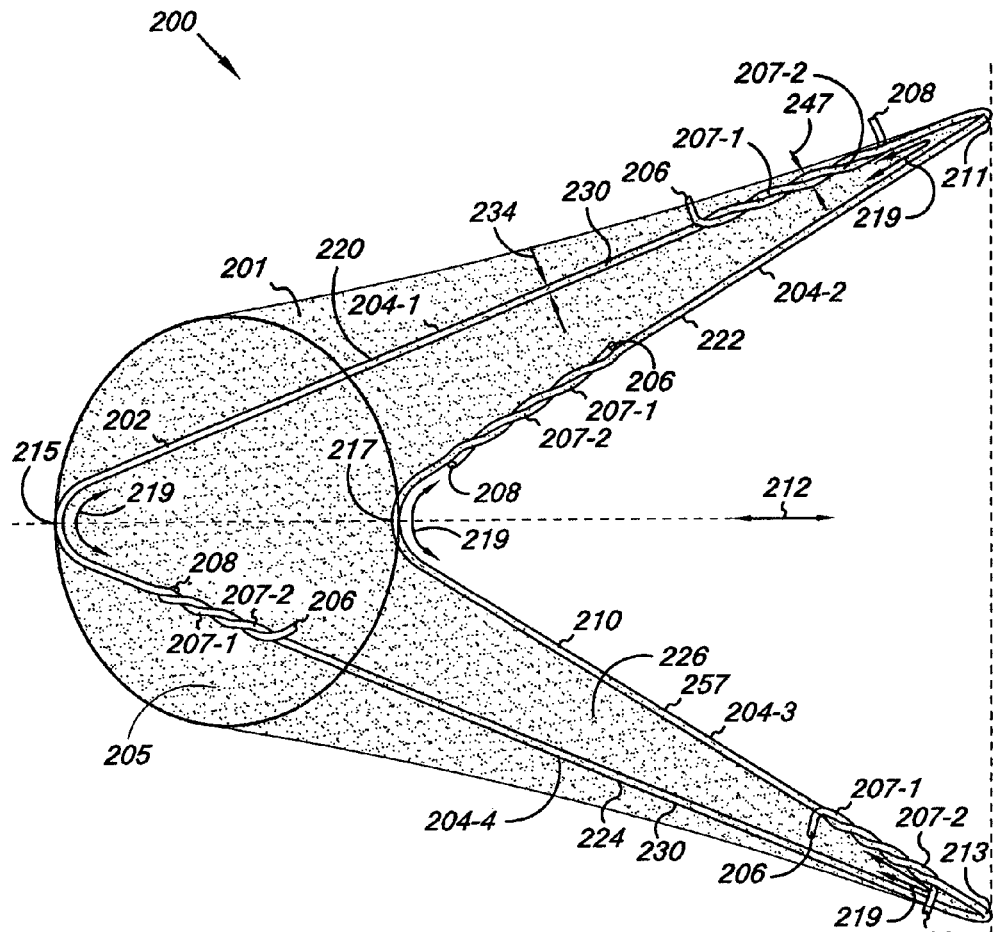
FIG. 2A illustrates an embodiment of a valve.
Figure 2B:
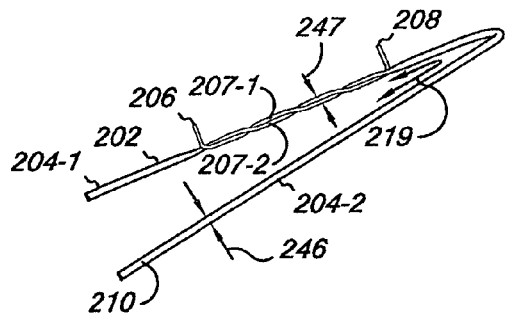
FIG. 2B illustrates an embodiment of a valve in a segment view.

Referring now to FIG. 2A, an embodiment of a valve 200 is illustrated that includes four (4) elongate members 204-1, 204-2, 204-3, and 204-4. As shown in FIG. 2A, each of the four (4) elongate members can include the first member end 206, the second member end 208, and the predetermined portion 207-1 and 207-2 adjacent the first and the second member ends 206 and 208 respectively. As discussed herein, the predetermined portion 207-1 and 207-2 adjacent the first and the second member ends 206 and 208 entwine to form the closed circumference of the frame 202. The frame 202 can have an outer surface 210, and the first and second member ends 206 and 208 can extend radially from the outer surface 210 and from the longitudinal central axis 212 of the frame 202.

Figure 3:
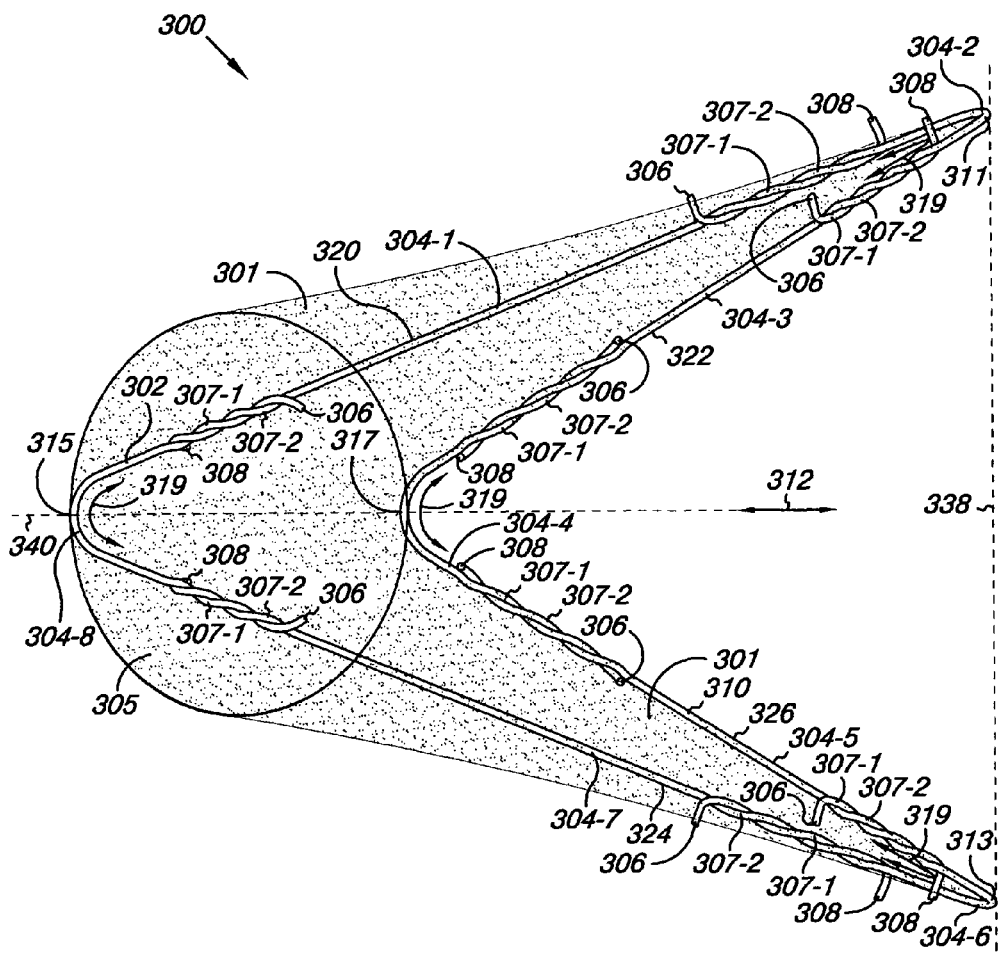
FIG. 3 illustrates an embodiment of a valve.

Referring now to FIG. 3, an embodiment of a valve 300 is illustrated that includes eight (8) elongate members 304-1 through 304-8. As shown in FIG. 3, each elongate member can have the first member end 306, the second member end 308, and the predetermined portion 307-1 and 307-2 adjacent the first and the second member ends 306 and 308 respectively. As discussed herein, the predetermined portion 307-1 and 307-2 adjacent the first and the second member ends 306 and 308 entwine to form a closed circumference of the frame 302. The frame 302 can have an outer surface 310, and the first and second member ends 306 and 308 can extend radially from the outer surface 310 and from the longitudinal central axis 312 of the frame 302.

Referring again to FIG. 1A, the cover 101 on the frame 102 can include surfaces defining a reversibly sealable opening 144 for unidirectional flow of a liquid through the valve 100. For example, the surfaces of the cover 101 can be deflectable between a closed configuration in which fluid flow through the lumen 105 can be restricted and an open configuration in which fluid flow through the lumen 105 can be permitted.

In one embodiment, the cover 101 can be located over at least the outer surface 110 of the frame 102 so as to cover the outer surface 110 of the frame 102 except for the first and second member ends 106 and 108 that protrude outward from the cover 101. In other words, the cover 101 extends over the outer surface 110 of the frame 102 so that the exposed portions of the outer surface 110 of the frame 102 are limited, or eliminated, except for the first and second member ends 106 and 108.

In an additional example, the cover 101 can extend between each of the elongate portions 120, 122, 124, and 126 and vertices 111, 113, 115 and 117 to completely surround the circumference of the frame 102. In an additional embodiment, the cover 101 can be located over at least an inner surface 130 of the frame 102. A further embodiment includes the cover 101 located over at least the outer surface 110 and the inner surface 130.

Figure 5A:
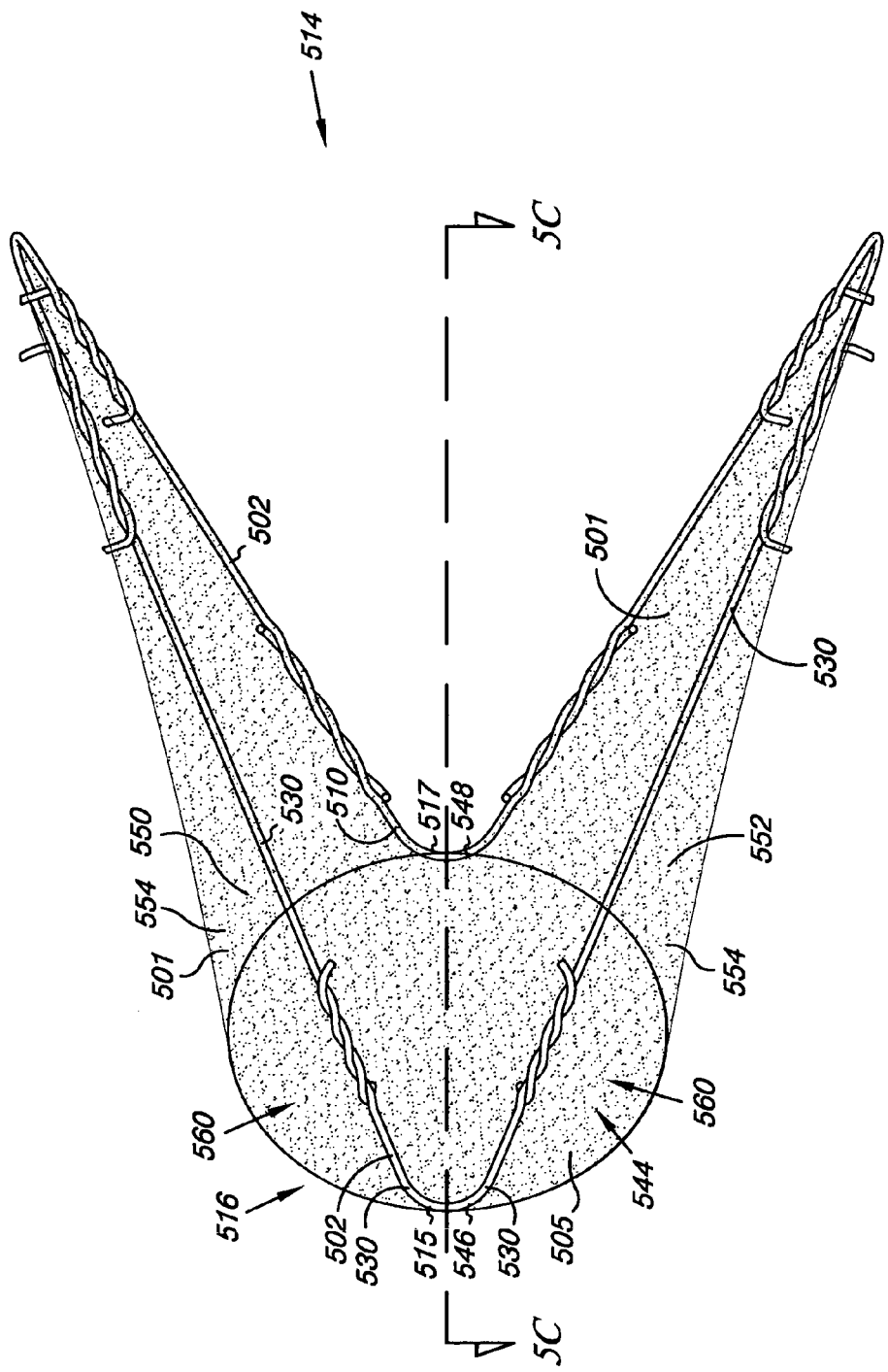
FIGS. 5A-5D illustrate an embodiment of a valve.
Figure 5B:
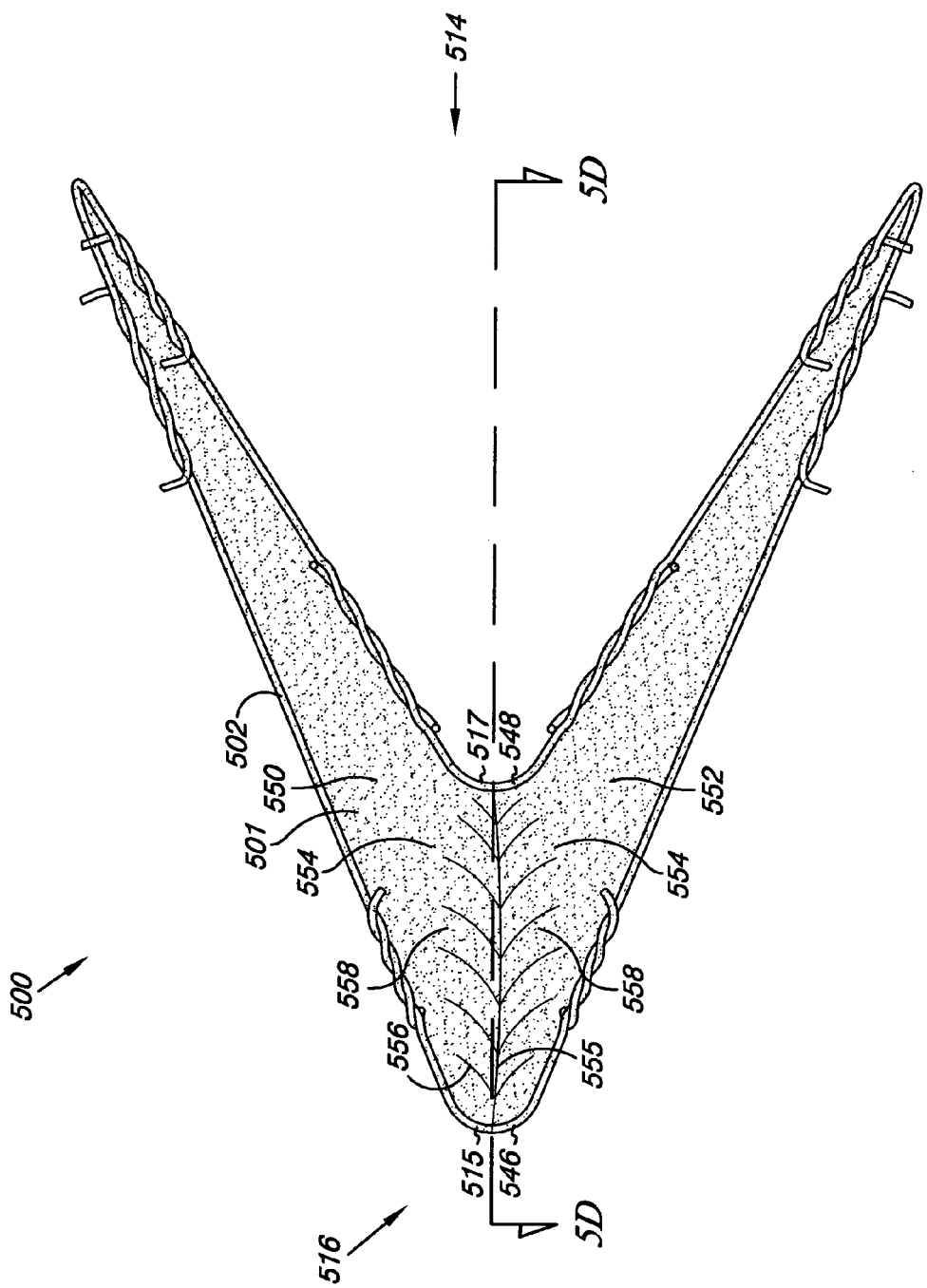
Figure 5D:
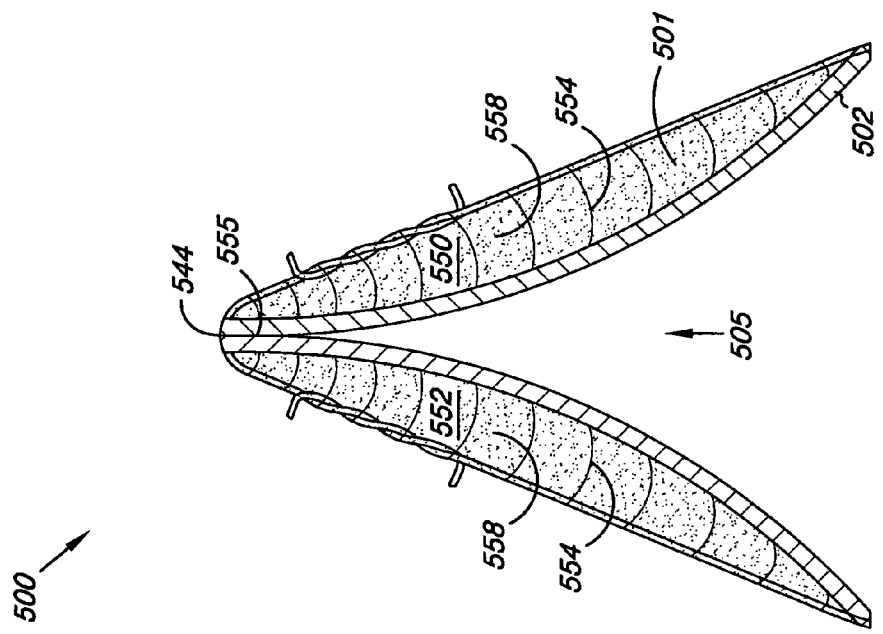
Figure 5C:
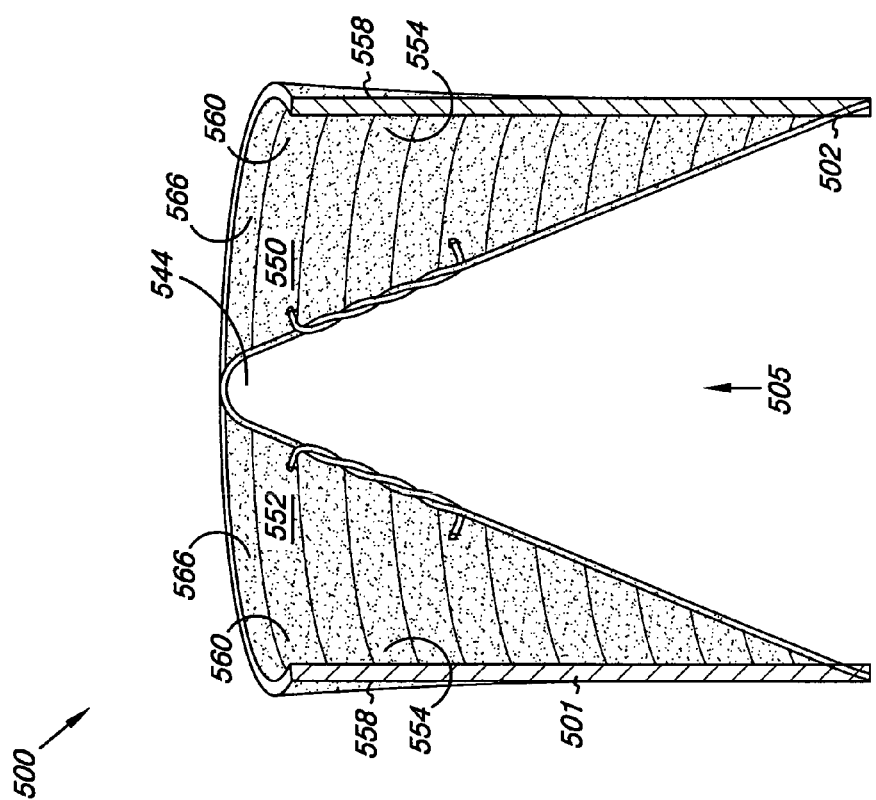

FIGS. 5A-5D illustrate an additional embodiment of the venous valve 500. FIGS. 5A and 5B provide a perspective illustration of valve 500 in an open configuration (FIG. 5A) and a closed configuration (FIG. 5B). FIGS. 5C and 5D provide a sectional view taken along cut lines 5C-5C and 5D-5D shown in FIGS. 5A and 5B, respectively, to more clearly illustrate the embodiment of the venous valve 500.

As discussed herein, cover 501 includes surfaces defining the reversibly sealable opening 544 for unidirectional flow of a liquid through the lumen 505. In the embodiment illustrated in FIGS. 5A and 5B, the cover 501 extends over at least a portion of the frame 502 to a first connection point 546 proximal the third vertex 515 and a second connection point 548 proximal the fourth vertex 517 on the frame 502, as the same have been described and illustrated in connection with FIGS. 1 and 2. In one example, the first connection point 546 and the second connection point 548 can be located at the third vertex 515 and the fourth vertex 517 of the frame 502. The cover 501 extends between the first connection point 546 and the second connection point 548 to provide a first valve leaflet 550 and a second valve leaflet 552. The first valve leaflet 550 and the second valve leaflet 552 can form the reversibly sealable opening 544 extending between the first connection point 546 and the second connection point 548. Thus, in the embodiment shown in FIG. 5A the first valve leaflet 550 and the second valve leaflet 552 form the reversibly sealable opening 544 extending between the third vertex 515 and the fourth vertex 517 of the frame 502.

As illustrated, the first valve leaflet 550 and the second valve leaflet 552 include a region 554 of the cover 501 that can move relative the frame 502. The region 554 of the cover 501 can be unbound (i.e., unsupported) by the frame 502 and extends between the first connection point 546 and the second connection point 548 of the valve 500. This configuration permits the reversibly sealable opening 544 to open and close in response to the fluid pressure differential across the valve leaflets 550 and 552.

For example, under antegrade fluid flow (i.e., positive fluid pressure) from the first end 514 towards the second end 516 of the valve 500, the first and second valve leaflets 550 and 552 can expand toward the inner surface 530 to create an opening through which fluid is permitted to move. In one example, the first valve leaflet 550 and the second valve leaflet 552 can each expand to define a semi-tubular structure when fluid opens the reversibly sealable opening 544. An example of the open configuration for the valve is shown in FIGS. 5A and 5C.

Under a retrograde fluid flow (i.e., negative fluid pressure) from the second end 516 towards the first end 514, the first and second valve leaflets 550 and 552 can move away from the inner surface 530 as the valve leaflets 550 and 552 begin to close valve 500. In one example, a pocket 556 exists between the frame 502 and each of the first and second valve leaflets 550 and 552. The pocket 556 allows fluid from the retrograde flow to develop pressure on a first major face 558 of the first and second valve leaflets 550 and 552, for example, as illustrated in FIG. 5B. In one embodiment, an example of a pocket 556 is illustrated in co-pending U.S. patent application Ser. No. 11/150,331, filed on Jun. 10, 2005 and entitled "Venous Valve System, and Method", which is incorporated herein by reference in its entirety.

As fluid pressure develops, the first and second valve leaflets 550 and 552 collapse, closing the reversibly sealable opening 544 to create a seal 555, thereby restricting retrograde fluid flow through the valve 500. In one example, the seal 555 can be created by the joining of a sealing surface 566 of the first and second valve leaflets 550 and 552, for example as illustrated in FIG. 5C. In the closed configuration, the first and second valve leaflets 550 and 552 can each have a concave structure when fluid closes the reversibly sealable opening 544. An example of a closed configuration for the valve is shown in FIGS. 5B and 5D.

In one embodiment, each of the first valve leaflet 550 and the second valve leaflet 552 includes sufficient excess material spanning frame 502 such that fluid pressure (e.g., antegrade flow) acting on a second major surface 560 of the first valve leaflet 550 and the second valve leaflet 552 forces the valve 500 into an open configuration.

As discussed above, the elastic regions of the frame also allow valve to elastically and repeatably travel between a collapsed state and an expanded state. For example, in the embodiments shown in FIGS. 6A and 6B, the valve 600 is illustrated in a collapsed state (FIG. 6A) and in an expanded state (FIG. 6B). As shown in FIGS. 6A and 6B, the valve 600 can travel between the collapsed and the expanded state along a radial travel path 661 (as shown in FIG. 6B), where there can be a change in a cross sectional area 663 of lumen 605. For example, the valve frame 602 can travel along the radial travel path 661 so as to change a width 665 of lumen 605. This can allow the valve 600 to react appropriately to the distension and contraction of a body lumen in which the valve 600 is placed.

In addition to the illustrated corner portions 119, the elastic regions can further include, but are not limited to, other shapes for the valve frame 102 that allow for repeatable travel between the collapsed state and the expanded state. For example, the elastic regions can include integrated springs having a circular or an elliptical loop configuration. Other shapes are also possible.

Referring again to FIGS. 1A-1B, valve 100 provides an embodiment in which the surfaces defining the reversibly sealable opening 144 provide a bi-leaflet configuration (i.e., a bicuspid valve) for valve 100. Although the embodiments described herein illustrate and describe a bi-leaflet configuration for the valve of the present invention, designs employing a different number of valve leaflets (e.g., tri-leaflet valve) are possible. For example, additional connection points (e.g., three or more) could be used to provide additional valve leaflets (e.g., a tri-leaflet valve).

The first valve leaflet 150 and the second valve leaflet 152 can have a variety of sizes and shapes. In one embodiment, each of the first valve leaflet 150 and the second valve leaflet 152 can have a similar size and shape. In other embodiments, each of the first valve leaflet 150 and the second valve leaflet 152 need not have a similar size and shape (i.e., the valve leaflets can have a different size and shape with respect to each other).

The first valve leaflet 150 and the second valve leaflet 152 each further include an arcuate edge 167 positioned adjacent each other along a substantially catenary curve between the connection point 146 and the second connection point 148 in the closed configuration of valve 100. Similarly, the arcuate edge 167 can define opening 144 when the valve 100 is in the open configuration. In one embodiment, the extent of the arcuate edge 167 imparted to the valve leaflet 150 and/or 152 can depend upon the elasticity of the material used for the valve leaflets. This aspect is illustrated in co-pending U.S. patent application Ser. No. 11/150,331, entitled "Venous Valve System, and Method", which is incorporated herein by reference in its entirety.

In an additional embodiment, in the open configuration the portion of the cover 101 forming the first valve leaflet 150 and the second valve leaflet 152 provides sufficient excess material spanning between the first connection point 146 and the second connection point 148 to allow the first and second major surfaces 158 and 160 to take on a semi-tubular structure 145, as shown in FIG. 1A, when fluid pressure opens the valve 100. In an additional embodiment, the arcuate edges 167 of valve 100 can open to approximately the full inner diameter of a body lumen. In an alternative embodiment, the arcuate edges 167 of valve 100 can open to provide a gap, or a space, between the arcuate edges 167 of valve 100 and the inner diameter of a body lumen. This aspect is illustrated in co-pending U.S. patent application Ser. No. 11/150,331, entitled "Venous Valve, System, and Method", which is incorporated herein by reference in its entirety.

Each of the second major surfaces 160 of the first valve leaflet 150 and the second valve leaflet 152 can further include a curve imparted thereto so as to provide the first major surface 158 with the pocket (illustrated as 556 in FIG. 5B). The pocket allows the first valve leaflet 150 and the second valve leaflet 152 to better collect retrograde fluid flow to urge the first valve leaflet 150 and the second valve leaflet 152 towards the closed configuration. For example, as retrograde flow begins, the first valve leaflet 150 and the second valve leaflet 152 respond by moving towards the center (e.g., towards 112) of valve 100. As the first valve leaflet 150 and the second valve leaflet 152 approach the center of the device the sealing surfaces 166 make sufficient contact to effectively close valve 100 and restrict retrograde fluid flow.

In an additional embodiment, the first valve leaflet 150 and the second valve leaflet 152 can include one or more support structures, where the support structures can be integrated into and/or onto the valve leaflets 150 and 152. For example, the first valve leaflet 150 and the second valve leaflet 152 can include one or more support ribs, as the same will be known and understood, having a predetermined shape. In one embodiment, the predetermined shape of the support ribs can include a curved bias so as to provide the first valve leaflet 150 and the second valve leaflet 152 with a curved configuration. Support ribs can be constructed of a flexible material and have dimensions (e.g., thickness, width and length) and cross-sectional shape that allows the support ribs to be flexible when the first valve leaflet 150 and the second valve leaflet 152 are urged into an open position, and stiff when the first valve leaflet 150 and the second valve leaflet 152 are urged into a closed position upon experiencing sufficient back flow pressure from the direction downstream from the valve. In an additional embodiment, support ribs can also be attached to valve frame 102 so as to impart a spring bias to the valve leaflets in either the open or the closed configuration.

In one embodiment, the material of the first valve leaflet 150 and the second valve leaflet 152 can be sufficiently thin and pliable so as to permit radially-collapsing of the valve leaflets for delivery by catheter to a location within a body lumen. The first valve leaflet 150 and the second valve leaflet 152 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), Dacron, polyethlylene (PE), polyethylene terephthalate (PET), silk, urethane, Rayon, Silicone, or the like. Possible biologic materials include, but are not limited to, autologous, allogeneic or xenograft material. These include explanted veins and decellularized basement membrane materials, such as small intestine submucosa (SIS) or umbilical vein.

As discussed herein, the cover 101 can be located over at least the outer surface 110 of the frame 102. In an additional embodiment, the cover 101 can also be located over at least the inner surface 130 of the frame 102, where the cover 101 can be joined to itself in the area between the elongate portions (e.g., between first elongate portion 120 and third elongate portion 124, and second elongate portion 122 and fourth elongate portion 126) so as to fully or partially encase the frame 102. Numerous techniques may be employed to laminate or bond cover 101 on the outer surface 110 and/or the inner surface 130 of the frame 102, including heat setting, adhesive welding, application of uniform force and other bonding techniques. Additionally, the cover 101 may be folded over the second end 116 of the frame 102 to provide the cover 101 on both the outer surface 110 and the inner surface 130. Cover 101 can also be joined to itself and/or the members according to the methods described in U.S. Patent Application Publication US 2002/0178570 to Sogard et al., which is hereby incorporated by reference in its entirety.

The cover 101 can also be coupled to the connection points so as to form the valve leaflets, as discussed herein. In one embodiment, the cover 101 can be in the form of a sheet or a sleeve of material, as discussed herein, which can be connected to the frame 102. Alternatively, the cover 101 can initially be in the form of a liquid that can be used to cast and/or form the cover over the frame 102. Other forms, including intermediate forms, of the cover 101 are also possible.

The cover 101 can be coupled to the frame 102, including the connection points 146 and 148, in a variety of ways so as to provide the various embodiments of the valve of the present invention. For example, a variety of fasteners can be used to couple the cover 101 to the frame 102 so as to form the valve 100. Suitable fasteners can include, but are not limited to, biocompatible staples, glues, sutures or combinations thereof. In an additional embodiment, the cover 101 can be coupled to the frame 102 through the use of heat sealing, solvent bonding, adhesive bonding, or welding cover 101 to either a portion of the cover 101 (i.e., itself) and/or the frame 102.

The cover 101, including the valve leaflets 150 and 152, may also be treated and/or coated with a number of surface or material treatments. For example, the cover 101 can be treated with one or more biologically active compounds and/or materials that may promote and/or inhibit endothelization and/or smooth muscle cell growth of the cover 101, including the valve leaflets 150 and 152. Similarly, the cover 101 may be seeded and covered with cultured tissue cells (e.g., endothelial cells) derived from a either a donor or the host patient which are attached to the valve leaflets 150 and 152. The cultured tissue cells may be initially positioned to extend either partially or fully over the valve leaflets 150 and 152.

Cover 101, in addition to forming valve leaflets 150 and 152, can also be capable of inhibiting thrombus formation. Additionally, cover 101 may either prevent or facilitate tissue ingrowth therethrough, as the particular application for the valve 100 may dictate. For example, cover 101 on the outer surface 162 may be formed from a porous material to facilitate tissue ingrowth therethrough, while cover 101 on the inner surface 164 may be formed from a material or a treated material which inhibits tissue ingrowth.

FIG. 7 illustrates one embodiment of a system 770. System 770 includes valve 700, as described herein, reversibly joined to catheter 772. The catheter 772 includes an elongate body 774 having a proximal end 776 and a distal end 778, where valve 700 can be located between the proximal end 776 and distal end 778. The catheter 772 can further include a lumen 784 longitudinally extending to the distal end 778. In one embodiment, lumen 784 extends between proximal end 776 and distal end 778 of catheter 782. The catheter 782 can further include a guidewire lumen 780 that extends within the elongate body 774, where the guidewire lumen 780 can receive a guidewire for positioning the catheter 782 and the valve 700 within a body lumen (e.g., a vein of a patient).

The system 770 can further include a deployment shaft 782 positioned within lumen 784, and a sheath 786 positioned adjacent the distal end 778. In one embodiment, the valve 700 can be positioned at least partially within the sheath 786 and adjacent the deployment shaft 782. The deployment shaft 782 can be moved within the lumen 784 to deploy valve 700. For example, deployment shaft 782 can be used to push valve 700 from sheath 786 in deploying valve 700.

FIG. 8 illustrates an additional embodiment of the system 870. The catheter 872 includes elongate body 874, lumen 884, a retraction system 888 and a retractable sheath 889. The retractable sheath 889 can be positioned over at least a portion of the elongate body 874, where the retractable sheath 889 can move longitudinally along the elongate body 874. The valve 800 can be positioned at least partially within the retractable sheath 889, where the retractable sheath 889 moves along the elongate body 874 to deploy the valve 800. In one embodiment, retraction system 888 includes one or more wires 895 coupled to the retractable sheath 889, where the wires are positioned at least partially within and extend through lumen 884 in the elongate body 874. Wires of the retraction system 888 can then be used to retract the retractable sheath 889 in deploying valve 800.

Figure 9:
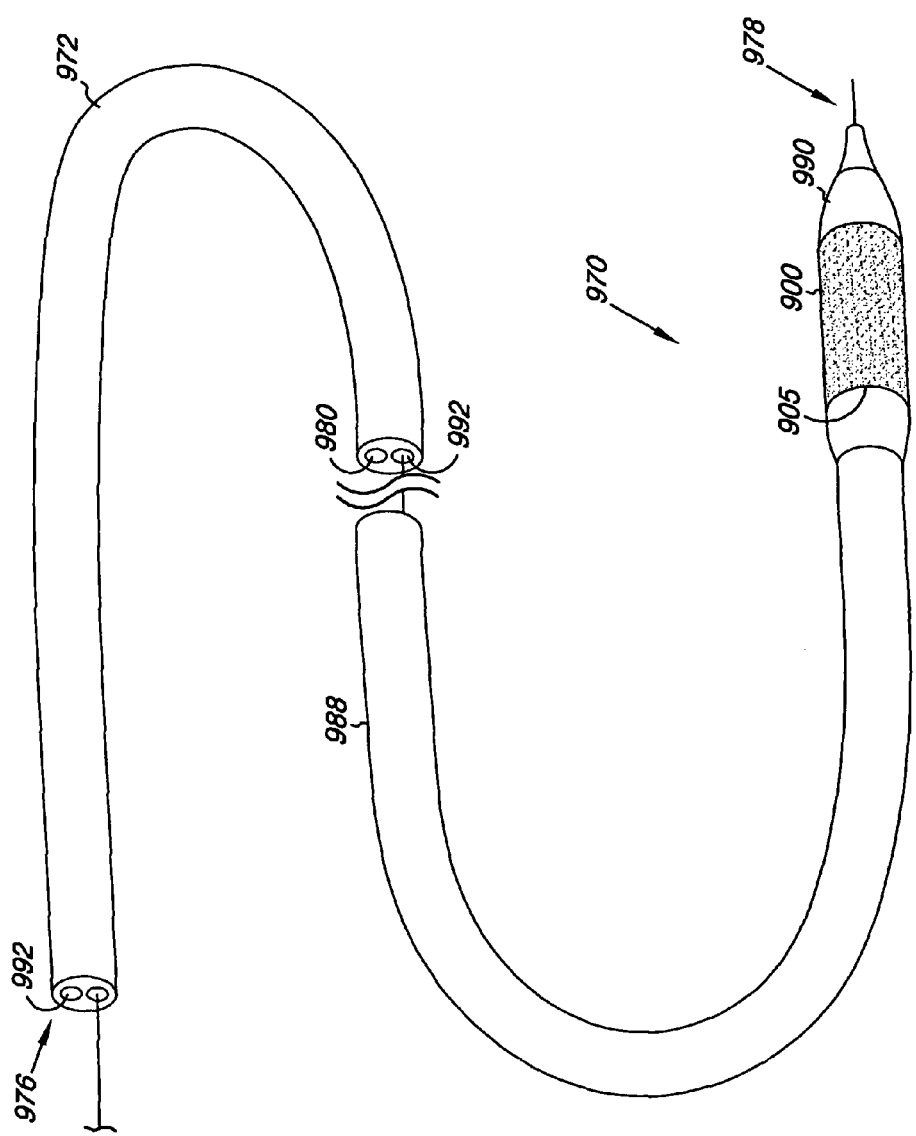
FIG. 9 illustrates an embodiment of a system that includes a valve.

FIG. 9 illustrates an additional embodiment of the system 970. The catheter 972 includes elongate body 974, an inflatable balloon 990 positioned adjacent the distal end 978, and a lumen 992 longitudinally extending in the elongate body 974 of the catheter 972 from the inflatable balloon 990 to the proximal end 976. In the present example, the inflatable balloon 990 can be at least partially positioned within the lumen 905 of the valve 900. The inflatable balloon 990 can be inflated through the lumen 992 to deploy the valve 900.

The embodiments of the present invention further include methods for forming the valve of the present invention, as discussed herein. For example, the valve can be formed from the frame and the cover over at least the outer surface of the frame, where the cover includes surfaces defining the reversibly sealable opening for unidirectional flow of a liquid through the lumen. In an additional example, the valve can be reversibly joined to the catheter, which can include a process of altering the shape of the valve from a first shape, for example an expanded state, to the compressed state, as described herein.

For example, the valve can be reversibly joined with the catheter by positioning valve in the compressed state at least partially within the sheath of the catheter. In one embodiment, positioning the valve at least partially within the sheath of the catheter includes positioning the valve in the compressed state adjacent the deployment shaft of the catheter. In an another embodiment, the sheath of the catheter functions as a retractable sheath, where the valve in the compressed state can be reversibly joined with the catheter by positioning the valve at least partially within the reversible sheath of the catheter. In a further embodiment, the catheter can include an inflatable balloon, where the balloon can be positioned at least partially within the lumen of the valve, for example, in its compressed state.

The embodiments of the valve described herein may be used to replace, supplement, or augment valve structures within one or more lumens of the body. For example, embodiments of the present invention may be used to replace an incompetent venous valve and help to decrease backflow of blood in the venous system of the legs.

In one embodiment, the method of replacing, supplementing, and/or augmenting a valve structure can include positioning at least part of the catheter including the valve at a predetermined location within the lumen of a body. For example, the predetermined location can include a position within a body lumen of a venous system of a patient, such as a vein of a leg.

In one embodiment, positioning the catheter that includes the valve within the body lumen of a venous system includes introducing the catheter into the venous system of the patient using minimally invasive percutaneous, transluminal catheter based delivery system, as is known in the art. For example, a guidewire can be positioned within a body lumen of a patient that includes the predetermined location. The catheter, including valve, as described herein, can be positioned over the guidewire and the catheter advanced so as to position the valve at or adjacent the predetermined location. In one embodiment, radiopaque markers on the catheter and/or the valve, as described herein, can be used to help locate and position the valve. For example, embodiments for positioning radiopaque markers on the catheter and/or the valve can be found in co-pending U.S. patent application Ser. No. 11/150, 331, filed on Jun. 10, 2005 and entitled "Venous Valve System, and Method", which is incorporated herein by reference in its entirety.

The valve can be deployed from the catheter at the predetermined location in a number of ways, as described herein. In one embodiment, valve of the present invention can be deployed and placed in a number of vascular locations. For example, valve can be deployed and placed within a major vein of a patient's leg. In one embodiment, major veins include, but are not limited to, those of the peripheral venous system. Examples of veins in the peripheral venous system include, but are not limited to, the superficial veins such as the short saphenous vein and the greater saphenous vein, and the veins of the deep venous system, such as the popliteal vein and the femoral vein.

As discussed herein, the valve can be deployed from the catheter in a number of ways. For example, the catheter can include the retractable sheath in which valve can be at least partially housed, as discussed herein. Valve can be deployed by retracting the retractable sheath of the catheter, where the valve self-expands to be positioned at the predetermined location. In an additional example, the catheter can include a deployment shaft and sheath in which valve can be at least partially housed adjacent the deployment shaft, as discussed herein. Valve can be deployed by moving the deployment shaft through the catheter to deploy valve from the sheath, where the valve self-expands to be positioned at the predetermined location. In an additional embodiment, the valve can be deployed through the use of an inflatable balloon.

Once implanted, the valve can provide sufficient contact and expansion force against the body lumen wall to prevent retrograde flow between the valve and the body lumen wall. For example, the valve can be selected to have a larger expansion diameter than the diameter of the inner wall of the body lumen. This can then allow valve to exert a force on the body lumen wall and accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the frame 102 and/or the cover 101 can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A venous valve, comprising:
a frame including an elongate member having a first member end, a second member end, a predetermined portion adjacent the first member end, and a predetermined portion adjacent the second member end, wherein the predetermined portions adjacent the first and the second member ends entwine to close a circumference of the entire frame, wherein the predetermined portions include a width different than the width of other portions of the frame such that where the predetermined portions are entwined the width of the entwined predetermined portions is no greater than the width of the other portions of the frame, and wherein the first and second member ends extend radially from an outer surface of the frame; and a cover on the frame, wherein the cover includes surfaces defining a reversibly sealable opening for unidirectional flow of a liquid through the valve.

2. The venous valve of claim 1, wherein the frame includes a first vertex and a second vertex relative a first end of the frame, wherein the first vertex and the second vertex are positioned opposite each other along a first axis.

3. The venous valve of claim 2, wherein the cover extends to at least the first vertex and the second vertex to form a first valve leaflet and a second valve leaflet between the first vertex and the second vertex.

4. The venous valve of claim 3, wherein the first valve leaflet and the second valve leaflet form the reversibly sealable opening extending between the first vertex and the second vertex.

5. The venous valve of claim 2, wherein the frame includes a third vertex and a fourth vertex at a second end of the frame relative the first and second vertex, the third vertex and the fourth vertex positioned opposite each other along a second axis.

6. The venous valve of claim 5, wherein the first, second, third, and fourth vertexes impart a radial expansion force when the frame is radially compressed.

7. The venous valve of claim 1, wherein the predetermined portions include a cross-sectional geometry different than a cross-sectional geometry of other portions of the frame.

8. The venous valve of claim 1, wherein the cover on the frame includes the cover over an outer surface of the frame.

9. The venous valve of claim 1, wherein the radial extension of the first and second member ends include a barb for attaching the frame to a body lumen wall.

10. A venous valve, comprising:
a frame including a plurality of elongate members, each elongate member having a first member end, a second member end, a predetermined portion adjacent the first member end, and a predetermined portion adjacent the second member end, wherein the predetermined portions adjacent the first and the second member ends entwine with predetermined portions of other of the plurality of elongate members to close a circumference of the entire frame, wherein the predetermined portions include a width different than the width of other portions of the frame such that where the predetermined portions are entwined the width of the entwined predetermined portions is no greater than the width of the other portions of the frame, and wherein the first and second member ends extend radially from an outer surface of the frame; and
a cover on the frame, wherein the cover includes surfaces defining a reversibly sealable opening for unidirectional flow of a liquid through the valve.

11. The venous valve of claim 10, wherein the frame includes a first vertex and a second vertex relative a first end of the frame, wherein the first vertex and the second vertex are positioned opposite each other along a first axis.

12. The venous valve of claim 11, wherein the frame includes a third vertex and a fourth vertex at a second end of the frame relative the first and second vertex, and positioned opposite each other along a second axis.

13. The venous valve of claim 12, wherein the first, second, third, and fourth vertexes impart a radial expansion force when the frame is radially compressed.

14. The venous valve of claim 10, wherein the plurality of elongate members of the frame include a number selected from the group including four elongate members and eight elongate members.

15. The venous valve of claim 10, wherein the radial extension of the first and second member ends functions to engage and attach to a body lumen.

16. The venous valve of claim 10, wherein the predetermined portions include a cross-sectional geometry different than a cross-sectional geometry of other portions of the frame.

17. A system, comprising:
a venous valve, wherein the venous valve includes:
a frame including a plurality of elongate members, each elongate member having a first member end, a second member end, a predetermined portion adjacent the first member end, and a predetermined portion adjacent the second member end, wherein the predetermined portions adjacent the first and the second member ends entwine with predetermined portions of other of the plurality of elongate members to close a circumference of the entire frame having an outer surface, wherein the predetermined portions include a width different than the width of other portions of the frame such that where the predetermined portions are entwined the width of the entwined predetermined portions is no greater than the width of the other portions of the frame, and wherein the first and second ends extend radially from the outer surface of the frame; and
a cover on the frame, wherein the cover includes surfaces defining a reversibly sealable opening for unidirectional flow of a liquid through the valve; and
a catheter including a proximal end and a distal end, the venous valve located between the proximal end and distal end of the catheter.

18. The system of claim 17, wherein the frame includes a first vertex and a second vertex relative a first end of the frame and positioned opposite each other along a common axis; and
the cover on the frame extends to at least the first vertex and the second vertex to form a first valve leaflet and a second valve leaflet between the first vertex and the second vertex, wherein the first valve leaflet and the second valve leaflet form the reversibly sealable opening extending between the first vertex and the second vertex.

19. The system of claim 17, wherein the catheter includes an elongate body having a lumen longitudinally extending to the distal end, a deployment shaft positioned within the lumen, and a sheath positioned adjacent the distal end, the venous valve positioned at least partially within the sheath and adjacent the deployment shaft, wherein the deployment shaft moves within the lumen to deploy the venous valve.

20. The system of claim 17, wherein the catheter includes an elongate body and a retractable sheath over at least a portion of the elongate body, the venous valve positioned at least partially within the retractable sheath, wherein the retractable sheath moves along the elongate body to deploy the venous valve.

21. The system of claim 17, wherein the catheter includes an inflatable balloon positioned adjacent the distal end and a lumen longitudinally extending in an elongate body of the catheter from the inflatable balloon to the distal end, the inflatable balloon at least partially positioned within a lumen of the venous valve, where the inflatable balloon inflates to deploy the venous valve.

22. The system of claim 17, wherein the cover extends over at least a portion of an inner surface of the frame, wherein the cover over the at least the portion of the inner surface extends to at least a first connection point and a second connection point on the frame to form a first valve leaflet and a second valve leaflet, wherein the first valve leaflet and the second valve leaflet includes a surface defining a reversibly sealable opening for unidirectional flow of a liquid through the valve.

23. A method of forming a venous valve, comprising:
providing a plurality of elongate members, each elongate member having a first member end, a second member end, a predetermined portion adjacent the first member end, and a predetermined portion adjacent the second member end;
entwining the predetermined portions of each elongate member with predetermined portions of other of the plurality of elongate members to close a circumference of an entire frame, wherein the predetermined portions include a width different than the width of other portions of the frame such that where the predetermined portions are entwined the width of the entwined predetermined portions is no greater than the width of the other portions of the frame;
extending the first and second member ends radially from an outer surface of the frame; and
providing a cover on the frame, wherein the cover includes surfaces defining a reversibly sealable opening for unidirectional flow of a liquid through the valve.

24. The method of claim 23, including reversibly joining the venous valve and a catheter.

25. The method of claim 24, wherein forming the venous valve includes:
providing the valve with a first vertex and a second vertex relative a first end of the frame and positioned opposite each other along a common axis; and
positioning the cover on the frame to extend to at least the first vertex and the second vertex to form a first valve leaflet and a second valve leaflet between the first vertex and the second vertex, wherein the first valve leaflet and the second valve leaflet form the reversibly sealable opening extending between the first vertex and the second vertex.

26. The method of claim 24, wherein reversibly joining the venous valve and the catheter includes positioning the venous valve at least partially within a sheath of the catheter.

27. The method of claim 26, wherein positioning the venous valve at least partially within a sheath of the catheter includes positioning the venous valve adjacent a deployment shaft of the catheter.

28. The method of claim 27, wherein the sheath includes a retractable sheath of the catheter.

29. The method of claim 24, wherein the catheter includes an inflatable balloon, the inflatable balloon at least partially positioned within a lumen of the venous valve; and
inflating the balloon to deploy the venous valve.

30. The method of claim 23, wherein the frame includes a first vertex and a second vertex relative a first end of the frame, wherein the first vertex and the second vertex are positioned opposite each other along a common axis; and
the cover extends to at least the first vertex and the second vertex to form a first valve leaflet and a second valve leaflet between the first vertex and the second vertex, wherein the first valve leaflet and the second valve leaflet includes a surface defining a reversibly sealable opening for unidirectional flow of a liquid through the valve.

31. The method of claim 23, wherein providing the cover includes extending the cover over at least a portion of the inner surface of the frame to at least a first connection point and a second connection point on the frame to form a first valve leaflet and a second valve leaflet, wherein the first valve leaflet and the second valve leaflet includes a surface defining a reversibly sealable opening for unidirectional flow of a liquid through the valve.

32. A method, comprising:
positioning at least part of a catheter including a venous valve at a predetermined location, wherein the venous valve includes:
a frame including a plurality of elongate members, each elongate member having a first member end, a second member end, a predetermined portion adjacent the first member end, and a predetermined portion adjacent the second member end, wherein the predetermined portions adjacent the first and the second member ends entwine with predetermined portions of other of the plurality of elongate members to close a circumference of the entire frame having an outer surface, wherein the predetermined portions include a width different than the width of other portions of the frame such that where the predetermined portions are entwined the width of the entwined predetermined portions is no greater than the width of the other portions of the frame, and wherein the first and second member ends extend radially from an outer surface of the frame; and
a cover on the frame, wherein the cover includes surfaces defining a reversibly sealable opening for unidirectional flow of a liquid through the valve; and
deploying the venous valve from the catheter at the predetermined location.

33. The method of claim 32, wherein the frame includes a first vertex and a second vertex relative a first end of the frame and positioned opposite each other along a common axis; and
the cover on the frame extends to at least the first vertex and the second vertex to form a first valve leaflet and a second valve leaflet between the first vertex and the second vertex, wherein the first valve leaflet and the second valve leaflet form the reversibly sealable opening extending between the first vertex and the second vertex.

34. The method of claim 32, wherein positioning at least part of the catheter at the predetermined location includes positioning at least part of the catheter within a vein of a leg.

35. The method of claim 32, wherein the catheter includes a retractable sheath, the venous valve at least partially housed within the retractable sheath, and deploying the venous valve from the catheter at the predetermined location includes retracting the retractable sheath of the catheter.

36. The method of claim 32, wherein the catheter includes a deployment shaft and a sheath, the venous valve at least partially housed within the sheath adjacent the deployment shaft, and deploying the venous valve from the catheter at the predetermined location includes moving the deployment shaft to deploy the venous valve from the sheath of the catheter.

37. The method of claim 32, wherein the frame includes a first vertex and a second vertex relative a first end of the frame, wherein the first vertex and the second vertex are positioned opposite each other along a common axis;
the cover extending to at least the first vertex and the second vertex to form a first valve leaflet and a second valve leaflet between the first vertex and the second vertex, wherein the first valve leaflet and the second valve leaflet includes a surface defining a reversibly sealable opening for unidirectional flow of a liquid through the lumen.

38. The method of claim 32, wherein the catheter includes an inflatable balloon, the inflatable balloon at least partially positioned within the lumen of the venous valve; and
deploying the venous valve includes inflating the balloon to deploy the venous valve.

* * * * *